United States Patent [19]

Gordon et al.

[11] Patent Number: 4,960,691
[45] Date of Patent: Oct. 2, 1990

[54] CHROMATOGRAPHIC TEST STRIP FOR DETERMINING LIGANDS OR RECEPTORS

[75] Inventors: Julian Gordon, Lake Bluff; Michael E. McMahon, Libertyville; Shanfun Ching, Vernon Hills, all of Ill.

[73] Assignee: Abbott Laboratories, Abbott Park, Ill.

[21] Appl. No.: 912,878

[22] Filed: Sep. 29, 1986

[51] Int. Cl.$^5$ .................... C12Q 1/68; G01N 33/543; G01N 33/548; G01N 33/558

[52] U.S. Cl. ........................................ 435/6; 422/56; 422/58; 422/61; 422/69; 422/70; 435/7; 435/805; 436/162; 436/501; 436/514; 436/518; 436/530; 436/807; 436/810

[58] Field of Search ................ 435/67, 805; 436/501, 436/518, 530, 807, 810, 162, 517; 422/56, 58, 69, 61, 70

[56] References Cited

U.S. PATENT DOCUMENTS

| | | | |
|---|---|---|---|
| 3,992,158 | 11/1976 | Przybylowicz et al. | 422/57 |
| 4,094,647 | 6/1978 | Deutsch et al. | 422/56 |
| 4,134,792 | 1/1979 | Boguslaski et al. | 435/7 |
| 4,168,146 | 9/1979 | Grubb et al. | 422/56 |
| 4,235,601 | 11/1980 | Deutsch et al. | 422/56 |
| 4,298,688 | 11/1981 | Kallies et al. | 435/14 |
| 4,328,133 | 5/1982 | Rosenfield et al. | 422/57 |
| 4,358,535 | 11/1982 | Flakow et al. | 435/5 |
| 4,361,537 | 11/1982 | Deutsch et al. | 422/56 |
| 4,391,904 | 7/1983 | Litman et al. | 436/537 |
| 4,425,438 | 1/1984 | Bauman et al. | 436/527 |
| 4,435,504 | 3/1984 | Zuk et al. | 435/7 |
| 4,517,288 | 5/1985 | Giegel et al. | 435/7 |
| 4,588,555 | 5/1986 | Provonchee | 422/56 |
| 4,855,240 | 8/1989 | Rosenstein et al. | 436/514 |

FOREIGN PATENT DOCUMENTS

| | | |
|---|---|---|
| 0063810 | 3/1982 | European Pat. Off. |
| 0120602 | 3/1984 | European Pat. Off. |
| 0164194 | 12/1985 | European Pat. Off. |
| 3445816 | 6/1986 | Fed. Rep. of Germany |
| 8702774 | 5/1987 | PCT Int'l Appl. |
| 2099578 | 1/1982 | United Kingdom |

OTHER PUBLICATIONS

H. Towbin et al., Immunoblotting and Immunoblotting-Current Status and Outlook, Journal of Immunological Methods, pp. 1-53, also Figures, Sep. 1984.

Gordon et al., Dot Immuno-Binding and Western Blotting as Diagnostic Tools, Immunoenzymetic Techniques, pp. 303-306, 1983.

Hawkes et al., A Dot Immunobinding for Monoclonal and Other Antibodies, Analytical Biochemistry, vol. 119, No. 1, Jan. 1982, pp. 142-147.

Rordorf et al., A Multidot Immunobinding Assay for Autoimmunity and the Demonstration of Novel Antibodies against Retroviral Antigens in the Sera of MRL-Mice, Journal of Immunological Methods, pp. 105-112, accepted Nov. 1982-printed 1983.

Van Hamont et al., Quantitative Immunochromatographic Strip Assay Method and Apparatus, Federal Register and the Patent and Trademark Official Gazette, Oct. 18, 1985, pp. 1-21.

Primary Examiner—Esther L. Kepplinger
Assistant Examiner—David A. Saunders
Attorney, Agent, or Firm—Donald L. Corneglio; Thomas D. Brainard; Jeffrey S. Sharp

[57] ABSTRACT

A test strip for analysis of analytes such as antigens, antibodies or polynucleotides employs a chromatographic medium and a solvent capable of transporting reagents and/or sample. Reagents are selected and disposed on the medium such that a labeled (first) reagent arrives at the detection (third) zone only after analyte is immobilized there and non-reactive sample componets have been transported beyond the detection zone. This sequential arrival is accomplished by the relative mobility of the reagent or sample; or by the site relationship of the zones. Preferably, the site relationship of the sample (second) zone and the label (first) zone is such that a plurality of pathways guide the sample and labeled reagent and any subsequent reagents to the detection zone in the recited order. Single and multiple pathway devices are disclosed.

33 Claims, 3 Drawing Sheets

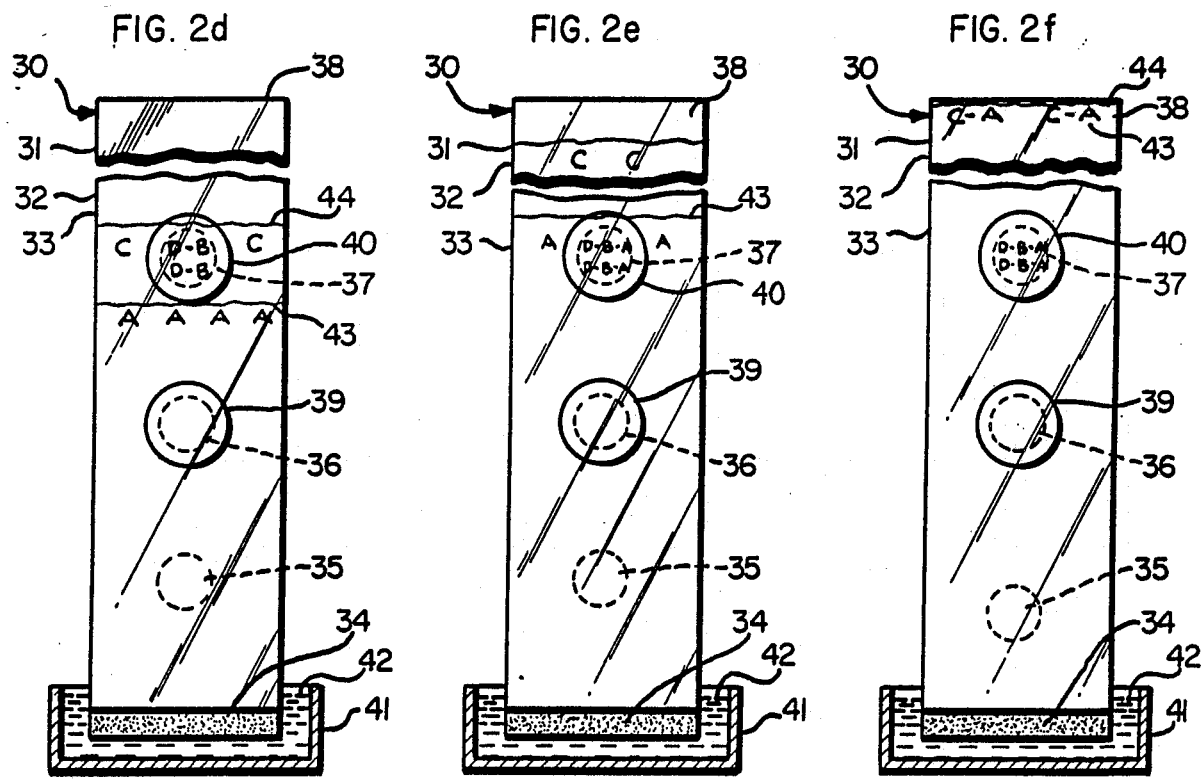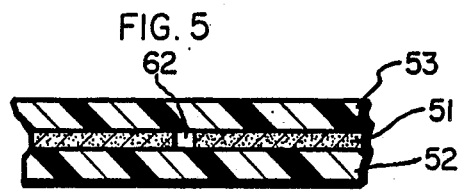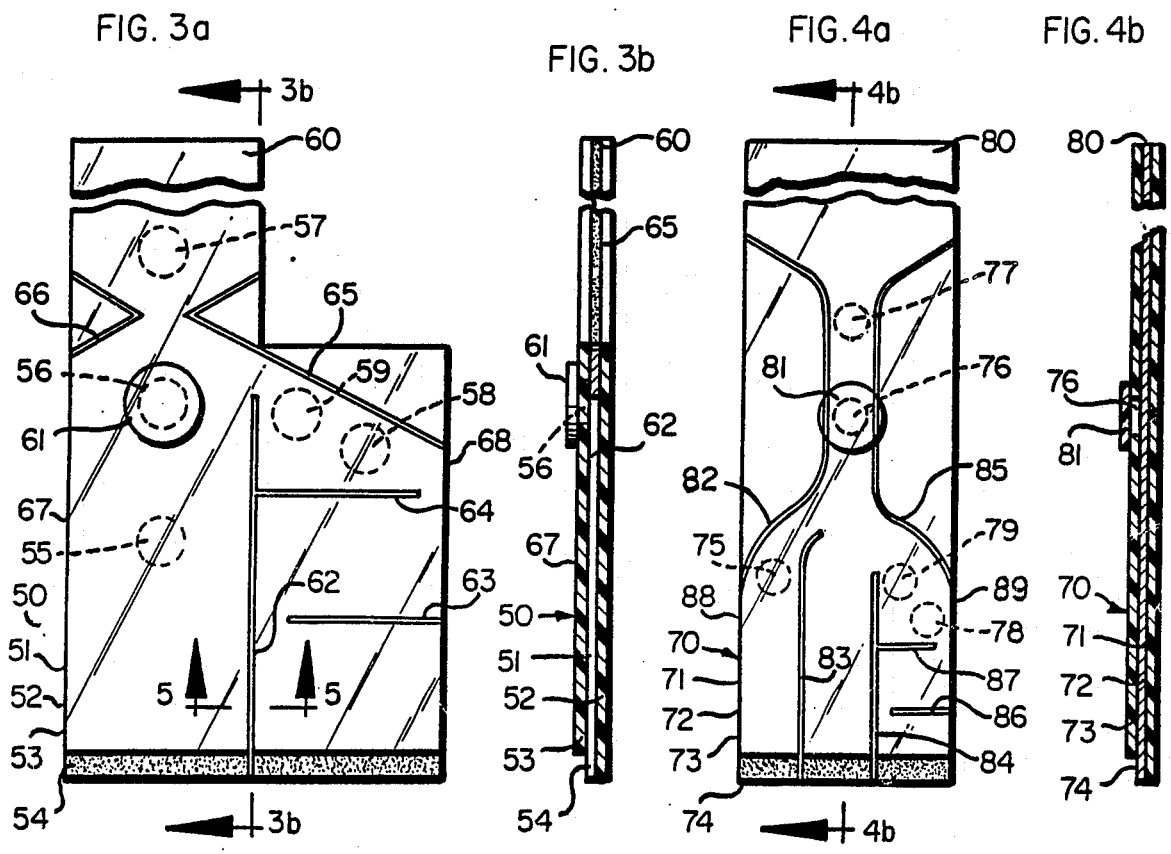

CHROMATOGRAPHIC TEST STRIP FOR DETERMINING LIGANDS OR RECEPTORS

BACKGROUND OF THE INVENTION

The present invention relates generally to solid phase methods for conducting specific binding assays upon sample fluids and more specifically to the use of chromatographic techniques in conducting such assays.

The use of specific binding assays has been found to be of great value in a variety of clinical applications. Various biological fluids and tissue samples can be analyzed for a wide variety of components such as drugs, hormones, enzymes, proteins, antibodies, DNA and RNA fragments and other biological material. Specific binding assays include those assays wherein an analyte is measured which is a member of a specific binding pair consisting of a ligand and a receptor. The ligand and the receptor are related in that the receptor specifically binds to the ligand, being capable of distinguishing the ligand from other sample constituents having similar characteristics. Immunological assays depend on reactions between immunoglobulins (antibodies) which are capable of binding with specific antigenic determinants of various compounds and materials (antigens). Specific binding assays may also involve DNA and RNA hybridization reactions wherein single strands of polynucleotides hybridize through hydrogen bond formation with strands of other polynucleotides comprising complementary sequences. Still other specific binding assays are known such as those involving hormone receptors which involve neither immunological reactions nor DNA hybridization.

Because the results of specific binding reactions are frequently not directly observable, various techniques have been devised for their indirect observation. Specific binding reactions may be observed by labelling of one of the members of the specific binding pair by well known techniques including radiolabelling and the use of chromophores, fluorophores and enzyme labels. Radiolabels, chromophores and fluorophores may be detected by use of radiation detectors, spectrophotometers or the naked eye. Where members of a specific binding pair are tagged with an enzyme label, their presence may be detected by the enzymatic activation of a reaction system wherein a compound such as a dyestuff, is activated to produce a detectable signal.

Immunological assays are of three general types. In competitive binding assays, labelled reagents and unlabelled analyte compounds compete for binding sites on a binding material. After an incubation period, unbound materials are washed off and the amount of labelled reagent bound to the site is compared to reference amounts for a determination of the analyte concentration in the sample solution. A second type of immunological assay is known as a sandwich assay and generally involves contacting an analyte sample solution to a surface comprising a first binding material immunologically specific for that analyte. A second solution comprising a labelled binding material of the same type (antigen or antibody) as the first binding material is then added to the assay. The labelled binding material will bind to any analyte which is bound to the first binding material. The assay system is then subjected to a wash step to remove labelled binding material which failed to bind with the analyte and the amount of labelled material remaining is ordinarily proportional to the amount of bound analyte.

A third type of immunological assay technique involves agglutination reaction techniques and is exemplified by well-known assays for blood antigens and serum types. Immunological cross-reactivity between antibodies within serum and antigens presented on red blood cell surfaces is indicated by the formation of a three dimensional cross-linked network of red blood cells and antibodies. The agglutination of the serum/red blood cell mixture results in the formation of a pellet which can be visible to the naked eye.

These various assay procedures were originally performed according to liquid phase immunochemistry techniques wherein enzyme and radiolabelled reactions were carried out in liquid solution in apparatus such as microtiter plates. More recently, techniques and procedures have been adapted for carrying out "solid" phase assays wherein enzymatic and immunological reactions are carried out in solution on damp porous solid substrates.

U.S. Pat. No. 4,328,183 to Rosenfield, et al. discloses a solid phase blood typing procedure whereby a monolayer of lysed red blood cell ghosts is covalently bound to the walls of a plastic tube. The monolayer is then contacted with a serum sample and immunoadsorption of the antibodies present in the sample by the bound red blood cell ghosts occurs when the antibodies are reactive with antigens presented by the cell membranes. The antibody sensitized monolayer of blood cells can then bind a second layer of blood cells carrying complementary antigen in an agglutination reaction. If the immunological type of both the cell monolayer and the antibody layer are known, the formation or non-formation of a second cell layer can be used to indicate the immunological type of the cells forming the second layer. Conversely, if the immunological specificity of the first cell layer is known, the ability to form a second cell monolayer with the same cells can be relied on as a means for determining whether or not there had been formed an immunosorbed layer of antibodies specifically reactive with the antigens of the first cell layer.

U.S. Pat. No. 4,168,146 to Grubb, et al., discloses the use of test strips for carrying out assertedly "solid phase" sandwich-type immunoassays. The strips are formed of bibulous carrier materials to which antibodies have been attached by adsorption, absorption or covalent bonding. Preferred test strip materials include cellulose fiber-containing materials such as filter paper, ion exchange paper and chromatographic paper. Also disclosed are uses of materials such as cellulose thin-layer chromatography discs, cellulose acetate discs, starch and three dimensional cross-linked materials such as Sephadex (Pharmacia Fine Chemicals, Uppsala Sweden). Immunoassays are carried out by wetting the test strips with measured amounts of an aqueous solution containing the suspected antigen. Antigen molecules within the test solution migrate by capillary action throughout the test strip, but because the bound antibodies retard the migration of the antigens for which they are specific, the extent of migration of the antigen molecules over a fixed time period is related as a function of the antigen concentration in the test solution. The antigen-containing areas of the diagnostic device are then indicated by the addition of labelled antibodies.

U.S. Pat. No. 4,517,288 to Giegel, et al. discloses methods for conducting solid phase immunoassays on inert porous materials. The patent discloses immunologically immobilizing a binding material within a specified zone of the porous material and applying the analyte to the zone containing the immobilized binding material. A labelled indicator material which will bind with the analyte is then applied to the zone where it will become immobilized in an amount correlated to the amount of analyte in the zone. A solvent is then applied to the center of the zone to chromatographically remove the unbound labelled indicator from the zone so that the amount of labelled indicator remaining in the zone may then be measured.

Deutsch, et al., U.S. Pat. No. 4,361,537 discloses test devices for the performance of specific binding assays such as radiolabelled competitive binding assays comprising a strip capable of transporting a developing liquid by capillarity which has a first zone for receiving a sample, a second zone impregnated with a first reagent capable of being transported by the developing liquid and a third zone impregnated with a third reagent. In addition, the devices comprise a measuring zone and a retarding element which may be either the second reagent or the material of the strip. The first reagent is capable of reacting with one of the group consisting of (1) the sample, (2) the sample and the second reagent, or (3) the second reagent in competition with the sample, to form a product in an amount dependent on the characteristic being determined. A sample is contacted with the first zone and the strip is then dipped into the developing liquid to bring about transport of the sample and the first reagent to form the reaction product. The retarding element slows transport of either the product or the first reagent (the moving reagent) to spacially separate the two and the amount of the moving element is then measured at the measurement location.

U.S. Pat. No. 4,435,504 to Zuk, et al. discloses a chromatographic immunoassay wherein the distance at which a border is formed from one end of the chromatograph is indicative of the quantity of analyte present in a sample. The analyte which is a member of a specific binding pair is immunochromatographed on a bibulous carrier to which its binding partner is nondiffusively bound and a variety of protocols are utilized to provide for delineation between the region to which the analyte is bound and the region free of analyte. According to one protocol, the analyte is chromatographed in the presence or absence of a labelled binding conjugate where the label is a member of an enzymatic signal producing system which includes one or more enzymes. If the labelled conjugate is not chromatographed with the analyte, the conjugate is applied to the chromatograph where it will bind to the chromatograph in proportion to the amount of analyte present. Similarly, if the labelled conjugate is chromatographed with the analyte, then the conjugate will bind to the analyte in proportion to the amount of analyte present at that position. The labelled conjugate can be an enzyme member of a signal producing system which can include chromophores, phosphors, fluorescers and chemiluminescers as well as coupled enzymatic signal systems. Where a coupled enzyme system is utilized, a second enzyme capable of reacting with the product of the first enzyme catalyzed reaction to form a detectable product may be chromatographed with the analyte solution or may be added to the test strip after chromatography of the analyte.

European Patent Application No. 164,194 (published Dec. 11, 1985) discloses improvements on the methods of Zuk, et al. in that transported chromatographic materials have substantially the same rate of traversal along the longitudinal edge of the chromatographic strip as along the body of the strip. This allows the chromatographic transport front to remain substantially flat rather than concave.

Of interest to the present patent application are two published patent applications of the inventor. U.S. Pat. No. 4,452,901 to Gordon discloses the use of porous nitrocellulose supports for immobilization of proteins. It is disclosed that such nitrocellulose sheets may be utilized in immunoassay procedures if the residual binding capacities of the nitrocellulose sheets are saturated by blocking treatment with one or more types of proteins, different from those immobilized and not cross-reactive with any of the antibodies subsequently used in the assay.

Of further interest to the background of the invention are the disclosures of Gordon, EPO Application 63,810, published Nov. 3, 1982, relating to devices for conducting immunological assays. The devices consist of a porous solid support containing a preselected array of delimited adsorption areas of antigens, antibodies or both, wherein residual adsorption sites on the substrate are saturated by protein blocking agents such as bovine serum albumin which do not cross-react with the antigens or antibodies employed in the assay. The porous supports are disclosed to have sufficient surface porosity to allow access by antibodies and surface affinity suitable for binding antigens. Such supports are disclosed to be selectable from a variety of natural and synthetic polymers and derivatives but are preferably nitrocellulose sheets 0.1 mm thick with pore size between about 0.15 $\mu$m and about 15 $\mu$m. Antigens or antibodies are applied to the porous solid support by direct contact followed by incubation with blocking agents. Assays for detection of unknown antigens or antibodies are then carried out through use of labelled antibodies which may also be anti-immunoglobulin antibodies. Results of single or multiple assays are determined by detection of the labelled antibodies.

Various specific binding assay techniques are also well known for the detection of specific DNA and RNA sequences. Such assays utilize nucleic acid hybridization procedures wherein complementary polynucleotide sequences of single stranded nucleic acid polymers recognize each other and interact to form a stable duplex structure. Southern, J. Mol. Biol. 98, 503–517 (1975) discloses procedures wherein DNA molecules separated by gel electrophoresis may be transferred from agarose electrophoresis gels to nitrocellulose filter paper. The DNA fragments may then be hybridized to radiolabelled RNA fragments for detection of particular sequences.

Falkow, et al., U.S. Pat. No. 4,358,535 discloses methods useful for the detection of DNA sequences associated with the infectious microorganism is isolated and fixed in a single stranded denatured form to an inert support such as nitrocellulose. A labelled polynucleotide probe specific for a DNA sequence characteristic of a pathogenic product suspected of being present in the clinical sample is contacted with the sample DNA under hybridizing conditions. The support is then washed to remove any unhybridized probe material and the presence of any remaining hybridized probe material is indicative of the presence of pathogen.

Dunn, et al., Cell, 12, 23–36 (1977) discloses an alternative hybridization procedure known as sandwich hybridization. According to this procedure, sample RNA is hybridized to defined DNA fragments which are bound to nitrocellulose filter paper supports such that the 3' or 5' end of the RNA protrudes as a single-stranded tail. DNA sequences complementary to the "tail" sequences can then be determined by treatment with specific fragments of labelled DNA under hybridizing conditions.

In addition to the various specific binding assay procedures known in the prior art, there also are known numerous assay procedures involving the diffusive or chromatographic transport of assay reagents. Forgione, U.S. Pat. No. 3,875,014 discloses solid phase test indicators for the determination of concentrations of the enzyme aspartate aminotransferase (AST) in sera utilizing a pair of reactions. In the first reaction AST catalyzes the reaction of L-aspartic acid and alpha ketoglutaratic acid to form oxaloacetate. In the second reaction, oxaloacetate reacts with a diazonium salt to form a colored reaction product. The test indicator of Forgione, comprises a pair of bibulous materials, adhered to each other with an adhesive which is selectively permeable to oxaloacetic acid. The first material is impregnated with the substrates L-aspartic acid and alphaketoglutaric acid. The second material is impregnated with a dried diazonium salt dyestuff. The device is contacted with sera which, if it contains AST, catalyzes the reaction of the substrates to form oxaloacetic acid. Oxaloacetic acid then diffuses through the adhesive barrier to the second strip and activates a color reaction with the diazonium salt which may be compared against standards.

Campbell, U.S. Pat. No. 3,893,808 discloses a test strip for the detection of lead contamination in unleaded motor fuels. The test strip comprises a paper strip having three zones. The first zone is impregnated with iodine, while the second zone is treated with a mixture of iodine and potassium iodide. A sample of motor fuel to be tested is applied to the strip and is transported by means of capillary action through the first and second zones to the third zone to which a dithizone indicator solution is then added. Any organic lead present in the motor fuel is converted to inorganic lead iodide on the surface of the strip and this is detected by reaction with the dithizone indicator to form a lead dithizonate complex with a characteristic color.

Alberty, et al., U.S. Pat. No. 3,895,914 discloses a test strip for the detection of barbituric acid and barbituric acid derivatives in a biological fluid. The strip comprises a bibulous paper strip having three zones. The first zone is impregnated with acid in order to acidify sample fluids applied thereto. The second zone is impregnated with alkaline buffered mercuric acetate capable of reacting to form a barbituratemercury complex. The third zone is impregnated with a mercury indicating compound such as diphenyl carbazone. A sample of fluid to be tested is applied to the first zone and the strip is dipped in solvent. Barbiturates present in the sample will react to form a barbiturate-mercury complex which will be transported to the third zone and will react with the mercury indicating compound.

Kallies, U.S. Pat. No. 4,298,688, discloses an assay device for the determination of glucose levels in biological fluids. The device comprises a paper test strip demarcated into a measuring zone which may be untreated, a reaction zone containing glucose oxidase, and a detection zone containing peroxidase and indicator substances such as o-tolidine and Orasol yellow. The material to be assayed is allowed to diffuse through the measuring zone to the reaction zone, wherein any glucose will react with the glucose oxidase, and then to the detection zone wherein a color reaction will take place, the degree of which depends on the extent of reaction carried out in the reaction zone. Water may be used to assist the diffusion of the test materials through the device and the test strip may also be enclosed within a glass capillary tube.

Fogt, et al., U.S. Pat. No. 4,444,193 discloses a quantitative test device for the measurement of chloride levels in sweat. The device, which is designed for use in screening for cystic fibrosis comprises a flat patch which when placed on the skin of a subject collects a fixed amount of sweat. The patch consists of two concentric circular reaction areas of chemically treated absorbant material. The sweat sample is introduced at the center of the inner circular reaction area which contains a chemical composition such as silver phosphate capable of reacting with all chloride in the sweat sample below a predetermined concentration in order to "screen out" a threshold quantity of chloride. The outer ring-shaped reaction area contains a chemical composition such as silver chromate which is brown in color and which reacts with any chloride reaching it to form white colored silver chloride and produce a color signal indicating the presence of chloride in excess of the predetermined threshold.

Of interest to the present invention is the disclosure of Wieland and Determann, J. Chromatog., 28, 2–11 (1967) relating to the use of Sephadex gels employed in a thin-layer chromatography format for separations of proteins. While Sephadex is not known as a conventional thin layer chromatography substrate and conventional thin layer chromatography is not practiced for the separation of proteins, highly cross-linked particles of Sephadex G-25 were used in ascending thin layer chromatography formats but a change in manufacture of Sephadex to bead form made ascending chromatography unworkable as the particles would not adhere and cohere satisfactorily. The use of large pore Sephadex types G-100 and G-200 in descending thin layer chromatography formats to the separation of proteins is also disclosed.

Morris, J. Chromatog., 16, 167–175 (1964) also discloses use of Sephadex type G-100 and G-200 plates in descending chromatography for proteins. The disclosure notes such transport is slow, however, stating that under "optimal operating conditions", human CO-haemoglobin should migrate only about 70 mm in approximately 4 to 5 hours.

Despite the great advances that have been made with respect to specific binding assay techniques in recent years, there still remain significant opportunities for improvement of these techniques. A particular limitation of current assay techniques is the requirement of numerous addition and wash steps. These steps, required to prevent undesired cross-reactions and remove excess reagents and interfering substances, complicate the procedure and effectively limit the type and level of sophistication of analytical procedures that may be carried out. Elimination or reduction of the number of washing and addition steps which must be carried out by technical personnel will not only reduce time and expense of conducting assays and analyzing assay results, but will also reduce the difficulty of automating result analysis. For these reasons, new systems involving solid phase assay devices requiring a minimum number of addition and washing steps are highly desired.

Such devices would preferably be susceptible to use in conducting assays for a wide variety of materials and would be capable of providing for the performance of a complex sequence of reactions in an essentially automatic manner.

SUMMARY OF THE INVENTION

The present invention provides novel methods and devices for conducting specific binding assay procedures upon sample fluids. These methods and devices require a minimum of washing and addition steps and are useful in carrying out qualitative and quantitative specific binding assays for a variety of analytes, including but not limited to, antibodies, antigens, DNA sequences, RNA sequences and other reactive chemical substances. In use of test devices according to the present invention, a reactant is selectively immobilized at a site on a chromatographic material and a plurality of reactants are brought sequentially into contact with the immobilized reagent and unreacted materials are physically removed therefrom, the timing and sequence being determined by the design of the device.

Specifically, the devices according to the invention comprise a test strip for the detection of an analyte in a sample comprising a length of chromatographic material having the capacity for rapid chromatographic solvent transport of non-immobilized reagents and reactive sample components by means of a selected chromatographic solvent. The strip includes a first end at which chromatographic transport begins, a second end at which chromatographic transport ends and a plurality of zones positioned between the two ends. The zones include a first zone (impregnated with a first reagent which is mobile in the solvent and capable of reaction with, and immobilization against solvent transport by the analyte when the analyte is in immobilized form), a second zone (for receiving the sample suspected of containing an analyte) and a third zone (positioned downstream of the first zone and impregnated with a second reagent which is immobilized against solvent transport and is capable of selective reaction with the analyte so as to render the analyte in an immobilized form in the third zone). The first and second zones are spaced sufficiently from the first end to permit contact of the first end, but not the first and second zones with the chromatographic solvent. The device is further characterized in that after the sample is received in the second zone and upon the first end being dipped into the chromatographic solvent, the relative mobility of the analyte and the first reagent or the site relationship between the second and third zones is such that the analyte is disposed and immobilized against solvent transport at the third zone prior to the first reagent reaching the third zone, whereby interfering sample components and non-analyte components of the sample which are reactive with the first reagent are cleared from the third zone by chromatographic solvent transport prior to chromatographic solvent transport of the first reagent to the third zone. The device optionally comprises means for detecting the first reagent at the third zone including fourth and fifth zones impregnated with third and fourth (indicator) reagents.

Assay procedures utilizing the devices are performed by (a) disposing the sample in the second zone; (b) dipping the first end into the chromatographic solvent for a time sufficient to chromatographically transport the analyte and the first reagent to the third zone, the relative mobility of the analyte and the first reagent or the site relationship between the second and third zones being such that the analyte is disposed at the third zone prior to the first reagent reaching the third zone, whereby interfering substances and nonanalyte components of the sample which are reactive with the first reagent are cleared from the third zone by the chromatographic solvent transport prior to the arrival of the first reagent and (c) detecting the presence of the first reagent in the third zone.

A significant aspect of the invention is the provision that the relative mobility of the analyte and the first reagent or the site relationship between the second or third zones are such that the analyte is disposed and immobilized against solvent transport at the third zone prior to the first reagent reaching the third zone so that interfering substances and nonanalyte components of the sample which are reactive with the first reagent are cleared from the third zone by chromatographic solvent transport prior to chromatographic solvent transport of the first reagent to the third zone. This feature, whereby a "wash" step is inherently carried out upon the third zone prior to contacting of the first reagent with that zone eliminates both a washing (of the third zone) step and an addition (of the first reagent) step. As a consequence of the ability to avoid manual washing steps it thus becomes possible to incorporate additional reagents upon the test strip and thus avoid manual addition steps. With the incorporation of additional reagents and the elimination of manual washing steps the devices of the present invention are thus capable of carrying out two or more reactions in sequence. It further becomes possible to utilize multiple chromatographic solvent transport pathways such that the sample, first reagent and any other materials such as indicator reagents can be transported according to a prearranged sequence with their separation maintained along partially non-coincident chromatographic solvent transport pathways. Multiple pathways may be formed so as to construct liquid microcircuitry which can be "programmed" to carry out a variety of multistep assay procedures by the sequential chromatographic solvent transport of various reagents to particular locations.

As a further aspect of the invention it has been found that thin-layer chromatographic substrate materials are particularly suitable for rapid chromatographic transport according to the present invention. While DNA and RNA sequences, proteins and large polypeptides including antibodies and various antigens have not conventionally been chromatographically transported on thin layer chromatography substrates, it has been found that rapid chromatographic solvent transport of such materials is possible when non-specific binding sites of the substrate have been suitably blocked as by treatment with non-specific protein blocking agents such as bovine serum albumin. While proteins, large polypeptides and other materials may be transported according to the invention by other chromatographic materials such as those utilized for paper chromatography, the use of thin layer chromatographic substrates is particularly preferred because of the improved speed and resolution afforded by the use of such materials.

BRIEF DESCRIPTION OF THE DRAWINGS

FIGS. 1a, 3a, 4a and 6a are front plan views of three different forms of the test device of the present invention;

FIGS. 1b, 3b, 4b and 6b are cross-sectional views of the test devices shown in FIGS. 1a, 3a and 4a respectively, taken along lines 1b—1b, 3b—3b, 4b—4b and 6b—6b;

FIGS. 2a—2f are front view plans of the device depicted in FIG. 1a at different points in time according to practice of methods of the invention; and FIG. 5 is a cross-sectional view of the test device of FIG. 3a taken along lines 5—5.

DETAILED DESCRIPTION OF THE INVENTION

General Description of the Devices

Figure 1A:
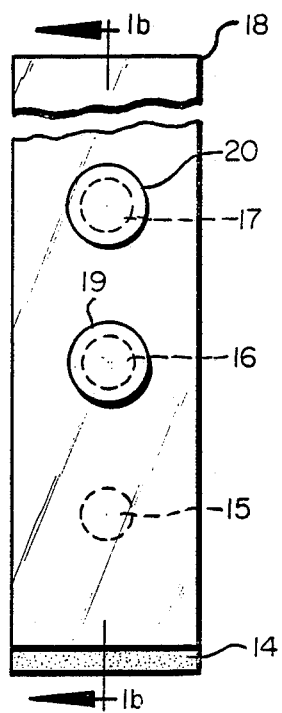

The devices of the present invention utilize a chromatographic solvent to sequentially transport analyte containing sample materials impregnated at a second zone and a first reagent impregnated at a first zone to a third zone wherein a second reagent which is capable of selective reaction with the analyte material so as to immobilize the analyte. By relying on the chromatographic solvent transport of the analyte and first reagent materials previously deposited upon the porous strip devices of the invention it is possible to avoid numerous addition and wash steps required in prior art assay systems.

A significant aspect of the invention is that the relative mobility of the analyte and the first reagent or the site relationship between the second or third zones is such that the analyte is disposed and immobilized against solvent transport at the third zone prior to the first reagent reaching the third zone and contacting the analyte. This aspect of the invention may be accomplished by making the second zone coincident with the third zone, that is, by depositing the sample directly onto the third zone. Alternatively, the mobility of the sample and the first reagent, or the design of the device, may be such that the first reagent and the analyzed interfering sample components and nonanalyte components of the sample which are reactive with the first reagent are prevented from contacting each other prior to immobilization of the analyte at the third zone.

A second significant aspect of the invention is interfering substances and non-analyte components of the sample which are reactive with the first reagent are cleared from the third zone by chromatographic solvent transport prior to arrival of the first reagent to the third zone. This feature, whereby a wash step is inherently carried out upon the third zone prior to contacting of the first reagent with that zone, eliminates the step of manually washing that zone after application of the sample to remove non-analyte components of the sample and materials which might interfere with or cross-react with reagents subsequently applied to the third zone. Elimination of this wash step also makes it possible to pre-apply chromatographically mobile reagent materials (such as the first reagent material) to the strip material during the process of manufacturing the device instead of requiring that such reagents be applied during the course of the assay procedure.

According to one embodiment of the invention, the second zone to which the sample material is applied and the third zone upon which the second reagent is immobilized may be coincident in order that the analyte may be immobilized against solvent transport at the third zone prior to the first reagent reaching the third zone. It is preferred, however, that the second and third zones be non-coincident in order that non-analyte components of the sample with little or no solubility in the chromatographic solvent will not remain in the third zone where they might interfere with or cross-react with the analyte, the second reagent or other reagents subsequently applied to the third zone. The allowance that small amounts of interfering sample components and non-analyte sample components which are reactive with the first reagent may not be susceptible to chromatographic solvent transport and may therefore react with the first reagent instead of being transported beyond the third zone is within the scope of the invention where such reaction does not interfere with detection of analyte materials at the third zone.

The identity of the reagents employed in practice of the invention will vary according to the identity of the analyte tested for. Where the analyte is an antigen or antibody, an immunological specific binding reaction between the analyte and the second reagent may be used to immobilize the analyte at the third zone. When the analyte is an antibody, the immobilized second reagent can be an antigen for which the antibody is specifically reactive and the first reagent can be a labelled antigen also specifically reactive with the analyte antibody or a labelled antiimmunoglobulin antibody specifically reactive with the analyte antibody. Where the analyte is an antigen, the immobilized second reagent can be an antibody specifically reactive with the antigen and the first reagent can be a labelled antibody or other specific binding material also specifically reactive with the antigen.

In cases where the analyte is a strand of DNA or RNA with a specific nucleotide sequence, the second reagent can be a single stranded DNA or RNA probe immobilized to the strip material which presents a nucleotide sequence capable of hybridizing with a first portion of the analyte nucleotide sequence so as to immobilize the analyte. The first reagent can then be a labelled specific binding material such as a labelled DNA or RNA probe with a nucleotide sequence capable of hybridizing with a second portion of the analyte nucleotide sequence so as to be immobilized by the analyte.

The assay methods and devices of the present invention need not be limited to those utilizing only two or even four reagents. Indeed, a significant advantage provided by the present methods and device is the ability to conduct multistep assay procedures with a minimum of manually conducted addition and washing steps by carrying out such washing steps "automatically" through chromatographic transport of the various analyzer and reactants and by pre-applying the reactants to the device during manufacture. Such multistep assay procedures can be conducted by incorporation of additional reagents and reagent zones onto the devices of the invention. Such reagents can be transported chromatographically to the third zone for reaction as part of the means for detection of the first reagent. According to one embodiment of the invention, third and fourth reagents may be incorporated upon the test device to provide a chemical substrate material and dye compound for reaction with an enzyme labelled first reagent. It is further envisioned that additional reagents may be chromatographically transported to other zones for reaction and that the products of such reactions may be immobilized or may be transported elsewhere for further reaction or detection. It is also envisioned that the device might be utilized for detection of multiple analytes within a single sample material. While it is intended that the invention provide for the elimination of manual washing and addition steps in the conduct of assays, it is also contemplated that certain manual washing and addition steps might be appropriate in the conduct of any particular assay procedures according to the invention.

The methods according to the present invention are characterized in that the flow of the chromatographic solvent which transports the analyte containing sample material to the third zone serves to clear (undesired) unfixed material from that zone. Such unfixed material includes sample components which might interfere with the reaction between the first reagent and the analyte as well as non-analyte sample components which might be reactive with the first reagent. In the case of immunological assays for the detection of specific antibodies in antibody containing fluids, those antibodies which are specifically reactive with the antigen material (second reagent) immobilized at the third zone will react with the antigen material and will themselves be immobilized at that zone. Non-analyte antibodies present in the sample which are not specifically reactive with the second reagent will not be immobilized at the third zone by the second reagent and will be chromatographically transported away from the third zone along with other components of the sample material. This is a particular advantage where the assay is a traditional "sandwich" assay and the first reagent is a labelled, species-specific antiimmunoglobulin antibody and failure to clear non-analyte antibodies from the third zone could result in false positive results. Failure to clear sample components which may interfere with the reaction between the analyte and the first reagent could result in false negative results. As one example, where the assay is a hybridization assay for the detection of specific DNA or RNA polynucleotide sequences, it is desired to separate sample nucleic acid material from non nucleic acid sample materials such as polysaccharides, polypeptides and proteins which can bind probes and interfere with the assay.

Devices according to the invention may make use of single or multiple chromatographic solvent transport pathways in order to carry out a variety of assay procedures. The simplest (single pathway) devices comprise a strip with a single transport pathway including a first end, a second end downstream of the first end, a first zone to which a labelled first reagent is deposited; a second zone at which the sample is received; and a third zone which is impregnated with a second reagent. The three zones are arranged along a single chromatographic solvent transport pathway such that the third zone lies downstream from the first and second zones and the second zone lies downstream from the first zone.

The simplest (multiple pathway) devices comprise two non-coincident pathways separately leading to the third zone. A first reagent is applied to a first zone on one pathway and later a sample is applied to the second zone on the other pathway. The chromatographic solvent, the strip materials of the two chromatographic transport pathways, the placement of the first and second zones and the compositions of the materials themselves are selected such that the sample materials will contact the third zone and any nonanalyte components of the sample which are reactive with the first reagent and any interfering substances are cleared from the third zone prior to chromatographic solvent transport of the first reagent to the third zone. Still more complex multiple transport pathway devices may be constructed wherein first, second and third zones are located along one pathway and fourth and fifth zones impregnated with an enzyme reaction substrate and a dye compound are located on a second partially non-coincident pathway leading to the third zone. Even more complex multicomponent systems may be constructed utilizing additional chromatographic transport pathways to maintain the separation between reagents and sample materials and in order to contact and react materials according to particular sequences.

Non-coincident and partially non-coincident chromatographic solvent transport pathways may be formed by a variety of means. Impermeable barriers may be formed between pathways to separate solvent transported materials until their transport to seleCted zones and areas. Such barriers may be formed by physically interpositioning an impermeable material between lengths of material comprising chromatographic solvent transport pathways. Alternatively, the chromatographic solvent transport material, such a nitrocellulose may be etched to form gaps between pathways. These gaps prevent lateral chromatographic solvent transport of materials from one side of the gap to the other and thus interaction of substances on one side of the gap with materials on the other.

Various embodiments of the invention including single, two, three and four pathway devices and their function are described herein.

Single Pathway Device

Figure 1B:
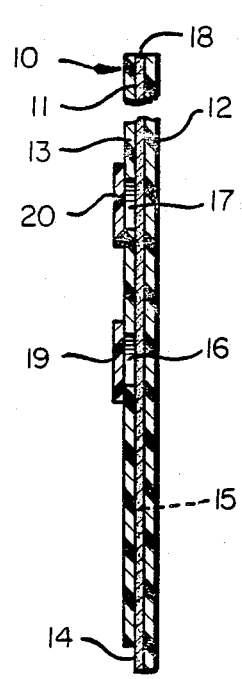
Figure 1C:
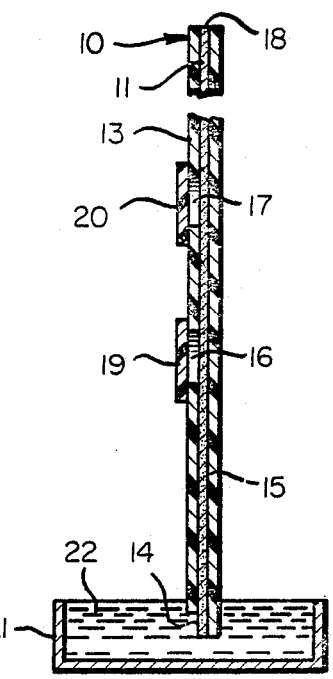
FIG. 1c is a cross-sectional view of the test device shown in FIG. 1a in contact with a volume of chromatographic solvent.

Referring to the drawing, FIGS. 1a, 1b and 1c depict a test device (10) for the detection of an analyte in a sample liquid comprising a length of chromatographic material (11) with a first end (14) at which chromatographic solvent transport begins and a second end (18) at which chromatographic solvent transport ends. The length of material (11) comprises a first zone (15), a second zone (16) and a third zone (17). The first zone (15) is impregnated with a first reagent which is mobile in the chromatographic solvent (21) and is capable of reaction with and immobilization against solvent transport by the analyte when the analyte is in immobilized form. The second zone (16) is downstream of the first zone (15) and provides a suitable site for receiving the sample to be analyzed. The third zone (17) is downstream of the second zone (16) and is impregnated with a second reagent which is immobilized against solvent transport and is capable of selective reaction with the analyte so as to render the analyte in an immobilized form. The device further comprises an inert support strip (12) to which the length of chromatographic material (11) is affixed. The device additionally comprises a cover plate (13) which is placed over the length of the chromatographic material (11) leaving exposed the first end (14) of the material. The cover plate (13) defines two openings corresponding to and leaving exposed the second zone (16) and the third zone (17). First and second removable tabs (19), (20) cover the second and third zones (16), (17) respectively. It should be noted for this and the other figures that the broken lines between the third zone (17) and second end (18) indicate an extended distance between those two features which provide for chromatographic solvent transport of all materials to or beyond the third zone (17) prior to the time when the chromatographic solvent front reaches the second end and chromatographic solvent transport terminates.

According to a procedure for use of device (10) of FIGS. 1a, 1b and 1c, the first tab (19) is removed from the device (10), a sample of the material to be tested is applied to the second zone (16) and the first tab (19) is replaced. The device (10) is then dipped at its first end (14) into a container (21) of chromatographic solvent (22). The chromatographic solvent (22) then progresses through the length of the chromatographic material (11) transporting a first reagent impregnated at the first zone (15) and the sample applied to the second zone (16) to the third zone (17). There, the immobilized second reagent material selectively reacts with analyte present in the sample so as to immobilize it. Non-analyte components of the sample are transported away from the third zone (17). The first reagent is then transported to the third zone (17) where it is immobilized against solvent transport by the analyte when any analyte is in immobilized form. Chromatographic solvent transport of the analytedepleted sample and first reagent continues until the chromatographic solvent (22) reaches the second end (18) of the material. The second tab (20) is then removed and dyestuffs or other reactive materials may be applied to the third zone (17) in order to detect the presence of the first reagent at the third zone (17).

FIGS. 2a-2f are front view plans of the device depicted in FIG. 1a. The figures, schematically represent the operation of a test device (30) for analysis of an analyte (B) in a sample comprising analyte (B) and non-analyte (C) materials whereby the device comprises a length of chromatographic material (31) with a first end (34) at which chromatographic solvent transport begins, a second end (38) at which chromatographic solvent transport ends, a first zone (35), a second zone (36) and a third zone (37). The first zone (35) is impregnated with a first reagent (A) which is mobile in chromatographic solvent (42) and capable of reaction with and immobilization against solvent transport by analyte (B) when said analyte (B) is in immobilized form. The third zone (37) is impregnated with a second reagent (D) which is immobilized against solvent transport and is capable of selective reaction with the analyte (B) so as to render the analyte (B) in an immobilized form in the third zone (37). The device further comprises an inert support strip (32) to which the length of chromatographic material (31) is affixed. The device additionally comprises a cover plate (33) which is placed over the material (31) leaving exposed the first end (14) of the material. The cover plate (33) defines two openings corresponding to and leaving exposed the second zone (36) and third zone (37). First and second removable tabs (39), (40) are placed on the cover plate (33) and cover the second and third zones (36), (37) respectively.

In use, the first tab (39) is removed from the cover plate (33) and a sample of the material to be analyzed comprising analyte (B) and non-analyte (C) materials is applied to the second zone (36). The first tab (39) is then replaced on the cover plate (33) covering the site of the second zone (36) in order to prevent the sample material from drying out.

Figure 2A:
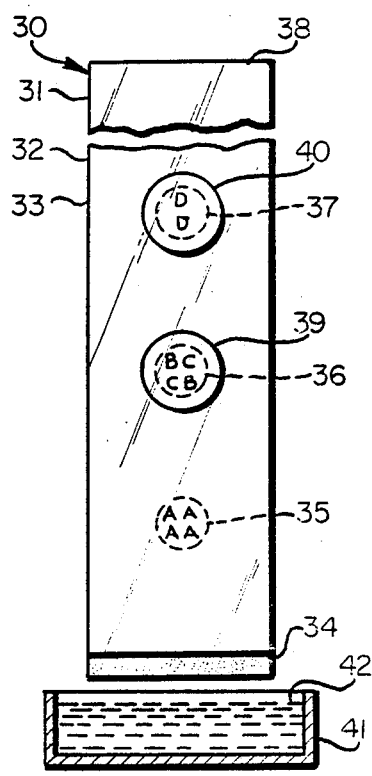
Figure 2B:
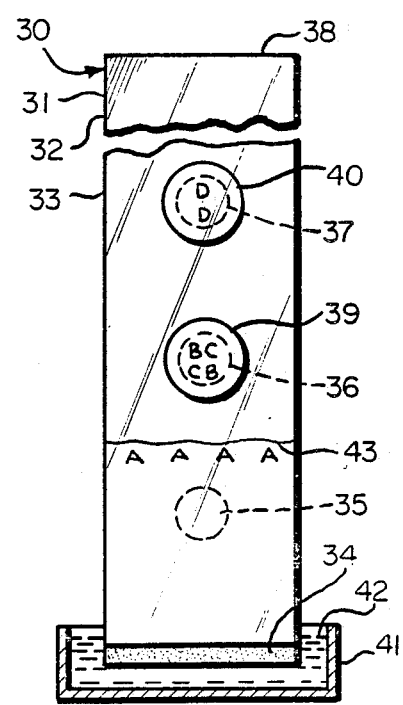

As shown in FIG. 2b, the first end (34) of the test device is dipped into a container (41) of chromatographic solvent (42) which then progresses through the chromatographic material (31) contacting the first zone (35) and transporting the first reagent (A) behind a chromatographic solvent front (43) downstream, toward the second end (38).

Figure 2C:
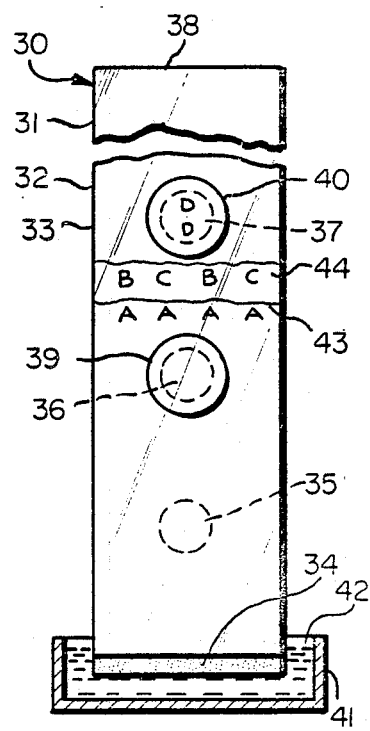

As shown in FIG. 2c, the chromatographic solvent front (43) contacts and passes through the second zone (36) where the sample liquid comprising analyte (B) and non-analyte (C) material have previously been deposited. It is preferred that the sample be liquid and that the second zone not be allowed to dry. Dried sample materials at the second zone may not be as rapidly solubilized in the solvent, with the result that the first reagent may contact and react with sample components prior to their transport to the third zone. (The "tetrode" four pathway device described below addresses this limitation and is suitable for use in some cases where dried samples are to be subject to analysis.) The sample liquid including the dissolved or suspended analyte (B) and non-analyte (C) materials are pushed along a sample transport front (44) ahead of the chromatographic solvent transport front (43) behind which the first reagent (A) is transported.

FIG. 2d illustrates that as the sample transport front (44) contacts and passes through the third zone (37), the second reagent (D), which is capable of selective reaction with the analyte (B), reacts with the analyte (B) so as to render it in an immobilized form at the third zone (37). The second reagent (D) is not specifically reactive with the nonanalyte components (C) of the sample liquid and these materials fail to be immobilized at the third zone (37).

FIG. 2e shows the sample transport front (44) and the non-analyte sample components (C) chromatography transported downstream from the third zone (37) toward the second end (38). At the same time, the chromatographic solvent front (43), behind which the first reagent (A) is transported, is contacted with the third zone (37) upon which the analyte (B) is immobilized. The first reagent (A) is capable of reaction with and immobilization against solvent transport by the analyte (B) when the analyte (B) is in immobilized form. Some of the first reagent (A) which is preferably present in excess concentrations is immobilized by the analyte (B) at the third zone (37). Any excess first reagent (A) continues to be transported by chromatographic solvent transport past the third zone (37).

As shown in FIG. 2f, the sample transport front (44) and the chromatographic solvent front (43) eventually reach the second end (38) of the device, at which point chromatographic solvent transport ends. Excess first reagent material (A) transported to the second end (38) can there move by diffusion and contact and react with non-analyte sample material (C) without effect on analytical accuracy.

The first reagent material (A) may be a labelled material which is directly detectable (such as a radiolabelled material) or one which is detectable by reaction with other materials. Where the first reagent (A) is directly detectable, the presence of a specific analyte (B) in a sample material may be detected by detection of the presence of the first reagent (A) at the third zone (37) such as with a radiation counter. Alternatively, where the first reagent (A) is not directly detectable, such as is the case with an enzyme-labelled reagent, additional reagents may be added to the third zone (37) for producing, e.g., a color reaction. Accordingly, the second tab (40) may be removed from the cover plate (33) and enzyme substrates and dye materials may be added to produce a color reaction in the presence of the immobilized first reagent (A).

Two Pathway Device (Diode)

FIGS. 3a and 3b depict a two pathway device referred to as a "diode" (50) for the detection of an analyte in a sample liquid. This device incorporates additional reagents which may be used for producing a detectable color signal by reaction with the enzyme label of the first reagent. The device comprises a length of chromatographic material (51) with a first end (54) at which chromatographic solvent transport begins and a second end (60) at which chromatographic solvent transport ends. The length of material is split by a center solvent barrier means (62) which with the left edge (67) defines a left-hand chromatographic solvent transport pathway and with the right edge (68) defines a right-hand chromatographic solvent transport pathway. The length of material comprises a first zone (55), second zone (56), third zone (57), fourth zone (58) and fifth zone (59). The first zone (55) is located in the left-hand chromatographic solvent transport pathway and is impregnated with a first reagent which is mobile in a chromatographic solvent and is capable of reaction with and immobilization against solvent transport by the analyte when the analyte is in an immobilized form. The second zone (56) is downstream of the first zone (55) along the left-hand chromatographic solvent transport pathway and provides a suitable site for receiving the sample to be analyzed.

The fourth zone (58) is located in the righthand chromatographic solvent transport pathway and is impregnated with a third reagent which is mobile in the chromatographic solvent. The fifth zone (59) is downstream of the fourth zone (58) along the right-hand chromatographic solvent transport pathway and is impregnated with a fourth reagent which is mobile in the chromatographic solvent. The third zone (57) which is impregnated with a second reagent which is immobilized against solvent transport is located downstream toward the second end (60) from the first (55), second (56), fourth (58) and fifth (59) zones.

In addition to the center solvent barrier (62) defining left-hand and right-hand chromatographic solvent transport pathways, the device comprises a first solvent baffle (63) and a second solvent baffle (64) which delay chromatographic solvent transport along the right-hand chromatographic solvent transport pathway by causing rising solvent to traverse a more circuitous route between the first end (54) and the second end (60). There also exists a right solvent barrier (65) and a left solvent barrier (66) which direct the chromatographic solvent transport of the sample materials and first, third and fourth reagents toward the third zone (57).

The device (50) further comprises an inert support strip (52) to which the length of chromatographic material is affixed and a cover plate (53) which is placed over the length of material (51) leaving exposed the first end (54) of the material. The cover plate (53) defines a hole corresponding to and leaving exposed the second zone (56). A tab (61) covers the second zone (56) and may be removed to apply sample materials or reagents to the second zone (56).

According to a procedure for the use of device (50) of FIGS. 3a and 3b, the tab (61) is removed from its position over the second zone (56) on the cover plate (53) and a liquid sample of the material to be analyzed is applied to the second zone (56). The tab (61) is then replaced over the second zone (56) in order to prevent the sample material from drying during the assay procedure. The device (50) is dipped at its first end (54) into chromatographic solvent which then progresses downstream toward the second end (60) along both the left-hand and right-hand solvent transport pathways. Chromatographic solvent transport along the right-hand solvent transport pathway is delayed as a consequence of the convoluted pathway imposed by the first (63) and second (64) baffles. Along the left-hand pathway, the chromatographic solvent transports the first reagent impregnated at the first zone (55) and the liquid sample material deposited at the second zone (56) to the third zone (57) without the first reagent contacting the sample material.

At the third zone (57), the immobilized second reagent selectively reacts with analyte present in the sample so as to immobilize it. Non-analyte components of the sample are chromatographically transported away from the third zone (57). The first reagent then contacts the third zone (57) where it is capable of being immobilized against solvent transport by the analyte when the analyte is in immobilized form.

At the same time, the chromatographic solvent progressing along the right-hand solvent transport pathway entrains and mixes the third and fourth reagents deposited at the fourth (58) and fifth (59) zones. The third and fourth reagents, illustratively comprising the enzyme catalyzed color signal means, are then channeled by the right solvent barrier (65) through the gap between the right solvent barrier (65) and the center solvent barrier (62) into the left-hand transport pathway. The majority of the sample material and first reagent will have by that time been transported past the narrow gap between the right solvent barrier (65) and the left solvent barrier (66), in order to minimize any contact of the first reagent with the third and fourth reagents which are specifically reactive with the first reagent to produce a detectable signal. Nevertheless, some amount of solvent including the sample and the first reagent will be transported into the right-hand solvent transport pathway where they will react with the third and fourth reagents producing a detectable signal at the point of their meeting. As chromatographic solvent transport continues, the third and fourth reagents are transported through the gap between the right solvent barrier (65) and the left solvent barrier (66) to the third zone (57). Upon contacting the third zone (57), the third and fourth reagents will react with any immobilized first reagent to produce a detectable signal indicating the presence of analyte.

Three Pathway Device (Triode)

FIGS. 4a and 4b depict an improved three pathway ("triode") device (70) for the detection of an analyte in a sample liquid. The device constitutes an improvement over the diode device of FIG. 3 in that it includes a third chromatographic solvent transport pathway which functions to help prevent the sample and first reagent from contacting the third or fourth reagents prior to those reagents contacting the third zone (77). The device comprises a length of chromatographic material (71) with a first end (74) at which chromatographic solvent transport begins and a second end (80) at which chromatographic solvent transport ends. The length of material is split by solvent impermeable barriers (82–85) into a left-hand solvent transport pathway defined by the left edge of the material (88), the first solvent barrier (82) and the second solvent barrier (83), a center solvent transport pathway defined by the second solvent barrier (86) and the third solvent barrier (87) and a righthand solvent transport pathway defined by the third solvent barrier (84), the fourth solvent barrier (85) and the right edge of the material (89). The three solvent transport-pathways combine to form an extension of the center solvent transport pathway which is defined by the first (82) and fourth (85) solvent barriers and the left (88) and right (89) edges of the material.

The length of chromatographic material comprises a first zone (75), second zone (76), third zone (77), fourth zone (78) and a fifth zone (79). The first zone (75) is located in the left-hand chromatographic solvent transport pathway, and is impregnated with a first reagent which is mobile in a chromatographic solvent and is capable of reaction with and immobilization against solvent transport by the analyte when the analyte is in immobilized form. The second zone (76) is downstream of the first zone (75) and located in the extension of the center solvent transport pathway defined by the first 82) and fourth (85) solvent barriers. The fourth zone (78) is located in the right-hand chromatographic solvent transport pathway and is impregnated with a third reagent which is mobile in the chromatographic solvent. The fifth zone (79) is downstream toward the second end (80) of the device along the right-hand chromatographic solvent transport pathway and is impregnated with a fourth reagent which is mobile in the chromatographic solvent. The third zone (77) is located downstream of the first (75), second (76), fourth (78) and fifth (79) zones in the extension of the center solvent transport pathway defined by the first (86) and fourth (85) solvent barriers.

The right-hand solvent transport pathway defined by the third (84) and fourth (85) solvent barriers and the right edge of the material (89) is the location of a first solvent baffle (83) and second solvent baffle (84) which delay chromatographic solvent transport along the right-hand chromatographic solvent transport pathway by causing rising solvent to traverse a more circuitous route between the first end (74) and the second end (80).

The device (70) further comprises an inert support strip (72) to which the length of chromatographic material (71) is affixed and a cover plate (73) which is placed over the length of material (71) leaving exposed the first end (74) of the material The cover plate (73) defines an opening corresponding to and leaving exposed the second zone (76). A tab (81) covers the second zone (76) and may be removed to apply sample materials or reagents to the second zone (76).

The improved device (70) of FIGS. 4a and 4b is used according to the same procedures as device (50) of FIGS. 3a and 3b. Specifically, the cover tab (81) is removed from its position over the second zone (76) on the cover plate (73) and a liquid sample of the material to be analyzed is applied to the second zone (76). The tab (81) is then replaced over the second zone (76) in order to prevent the sample material from drying during the assay procedure. The device (70) is dipped at its first end (74) into chromatographic solvent which then progresses downstream toward the second end along the left-hand, center and right-hand solvent pathways. Chromatographic solvent transport along the right-hand solvent transport pathway is delayed as a consequence of the convoluted pathway forced upon it by the first (83) and second (84) baffles. Along the left-hand pathway, the chromatographic solvent transports the first reagent impregnated at the first zone (75) and the liquid sample material deposited at the second zone (76) to the third zone (77). The chromatographic solvent is also transported along the center chromatographic solvent transport pathway with the effect that it reaches the junction of the left-hand chromatographic solvent transport pathway and right-hand solvent transport pathway and prevents back flow of the first reagent into the right-hand solvent transport pathway where the fourth and fifth zones are impregnated with the third and fourth reagents specifically reactive with the first reagent so as to produce a color signal. It is in minimizing this backflow and consequent prevention of premature reaction that device (80) of FIGS. 4a and 4b represents an improvement over the device (60) of FIGS. 3a and 3b. In that device (60), a portion of the first reagent material, which is specifically reactive with the fourth (58) and/or fifth (59) reagents, can flow back into the right-hand transport pathway of that device with the effect that quantities of the first, third and fourth reagents are consumed prematurely and spurious signals are produced which may not necessarily be associated with detection of an analyte.

Chromatographic solvent transport continues with the sample and first reagent transported toward the third zone (77). The first (82) and fourth (85) solvent barriers are designed so as to concentrate flows of reagents to the third zone. At the third zone (77), the immobilized second reagent selectively reacts with analyte present in the sample so as to immobilize it while non-analyte components of the sample are not immobilized and are transported away from the third zone (77). The first reagent then contacts the third zone (77) where it is immobilized against solvent transport by the analyte when the analyte is in immobilized form. At the same time, the chromatographic solvent progressing along the right-hand solvent transport pathway entrains the third reagent deposited at the fourth zone (78) and the fourth reagent deposited at the fifth zone (79). The third and fourth reagents are channeled by the fourth solvent barrier (85) into the extension of the center solvent transport pathway after the first reagent has been transported into the extension. As chromatographic solvent transport continues, the third and fourth reagents are transported to the third zone (57) where they reacting with any immobilized first reagent to produce a detectable color signal.

Referring to the drawing, FIG. 5 depicts a cross-section view of the test device (50) of FIG. 3a taken along lines 5—5. The figure illustrates the material having capillarity (51) through which the chromatographic solvent transport takes place. The material is sandwiched between an inert support strip (52) and an inert cover sheet (53) through which solvent transport may not occur. Two portions of the material (51), representing separate solvent transport pathways, are separated by the center solvent barrier (62) which is impermeable to solvent transport. The solvent barrier (62) may be an impermeable material or it may represent an air or gas-filled gap in material (51) of sufficient width that solvent chromatographic transport will not take place across the gap.

Four Pathway Device (Tetrode)

Figure 6A:
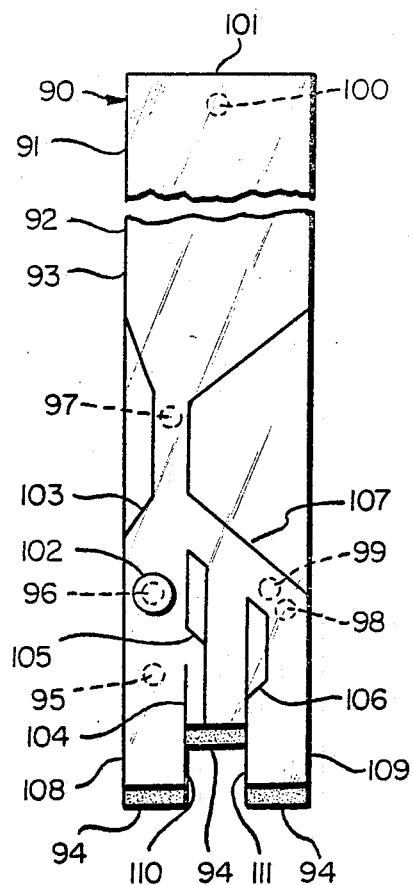
Figure 6B:
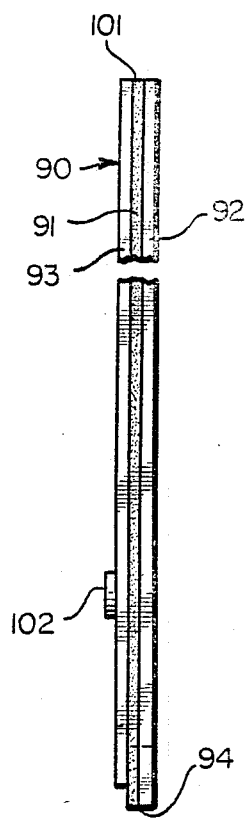

FIGS. 6a and 6b depict an improved four pathway ("tetrode") device (90) for the detection of an analyte in a sample liquid. The device constitutes an improvement over the triode devices in FIG. 4 in that the arrangement of the four solvent transport pathways not only prevents premature contact of the first reagent with the third or fourth reagents but also functions to prevent the first reagent from contacting the sample prior to the sample contacting the third zone (97).

The device comprises a length of chromatographic material (91) with a first end (94) at which chromatographic solvent transport begins and a second end (101) at which chromatographic solvent transport ends. The first end of the device (94) is indented at its center, defining a gap between, the left and right-hand sides of the device. The length of material is further split by solvent impermeable barriers (103-107) into four chromatographic solvent transport pathways which merge midway along the length of the device to form a center chromatographic solvent transport pathway in which the third zone (97) is located. A left-hand chromatographic solvent transport pathway is defined by the left edge of the device (108) and the first solvent barrier (103) on one side and the left gap edge (110) of the device and the second and third (104-105) solvent barriers on the other. A righthand chromatographic solvent transport pathway is defined by the right edge of the device (109) and the fifth solvent barrier (107) on one side and the right gap edge (111) of the device and the fourth (106) solvent barrier on the other. Downstream of the gap and between the left and right-hand solvent transport pathways are defined left-center and right-center solvent transport pathways. The left-center pathway is defined by the second solvent barrier (104) on one side and the third solvent barrier (105) and leads from the first end (94) atop the gap to the left-hand solvent pathway. The right-center pathway is defined by the third solvent barrier (105) on one side and the fourth solvent barrier (106) on the other and leads from the first end (94) atop the gap to the right-hand solvent transport pathway.

The length of material comprises a first zone (95), second zone (96), third zone (97), fourth zone (98), fifth zone (99) and sixth zone (100). The first zone (95) is located in the left-hand chromatographic solvent transport pathway, and is impregnated with a first reagent which is mobile in a chromatographic solvent and is capable of reaction with and immobilization against solvent transport by the analyte when the analyte is in immobilized form. The second zone (96) is located in the left-hand solvent transport pathway downstream of the first zone (95) and the point where the left-center solvent transport pathway merges with the left-hand transport pathway. The fourth zone (98) is located in the right-hand chromatographic solvent transport pathway and is impregnated with a third reagent which is mobile in the chromatographic solvent. The fifth zone (99) is located downstream toward the second end (101) of the device along the right-hand chromatographic solvent transport pathway and is impregnated with a fourth reagent which is mobile in the chromatographic solvent. The third zone (97) is located downstream of the first (95), second (96), fourth (98) and fifth (99) zone, in the extension of the center solvent transport pathway defined by the first (103) and fifth (107) solvent barriers. The sixth zone (100) is located downstream of the third zone (97) close to the second end (101) and is impregnated with a fifth reagent which indicates the presence of solvent at the second end.

The device (90) further comprises an inert support strip (92) to which the length of chromatographic material (91) is affixed and a cover plate (93) which is placed over the length of material (91) leaving exposed the first end (94) of the material. The inert support strip (92) and the cover plate (93) are impermeable to solvent and surround the chromatographic material such that it is impermeable along its edges and may be wetted with solvent only where the cover plate exposes the chromatographic material at the first end (94). The cover plate (93) further defines an opening corresponding to and leaving exposed the second zone (96). A tab (102) covers the second zone (96) and may be removed to apply sample materials or reagents to the second zone (96).

The improved device (90) of FIGS. 6a and 6b is used according to the same procedures as devices (50) and (70) of FIGS. 3a, 3b, 4a and 4b. Specifically, the tab (102) is removed from its position over the second zone (96) on the cover plate (93) and a liquid sample of the material to be analyzed is applied to the second zone (96). The tab (102) is then replaced over the second zone (96) in order to prevent the sample material from drying during the assay procedure. The device (90) is dipped into chromatographic solvent to a depth such that solvent contacts the first end (94) for all four solvent transport pathways but wherein the cover plate is designed such that solvent transport begins further downstream toward the second end on the second and third solvent transport pathways than the first and fourth pathways. The solvent then progresses downstream toward the second end along the left-hand, left-center, right-center and right-hand solvent pathways.

Chromatographic solvent transport along the left-center solvent transport pathway progresses such that solvent is transported onto the left-hand chromatographic solvent transport pathway between the first zone (95) and second zone (96). Because the leftcenter transport pathway is shorter than the left-hand solvent transport pathway, this solvent reaches the area between the first and second zones before solvent progressing from the first end (94) of the left-hand pathway reaches that area. The solvent introduced from the left-center pathway thus acts to separate the first reagent deposited at the first zone (95) from sample materials deposited at the second zone (96). The solvent contacts the sample materials at the second zone solubilizes them and transports them downstream toward the second end (101). At the same time, the solvent contacts the first reagent impregnated at the first zone (95) and transports this "upstream" toward the first end (94) until it meets the solvent front progressing "downstream" from the first end (94). The first reagent is then transported downstream toward the third zone. (101) but separated from the sample materials by the mass of solvent introduced by the left-center solvent transport pathway. The mass of fluid introduced from the left-center solvent transport pathway is also useful in some cases where the sample material has dried. The mass of solvent often provides enough time to solubilize the material and transport it while maintaining separation between the sample and the first reagent.

Chromatographic solvent transport along the right-center solvent transport pathway progresses such that solvent is transported to the junction of the right-center transport pathway and the right-hand transport pathway. Because the right-center pathway is shorter than the right-hand pathway and the right-hand pathway is constricted between the fourth solvent barrier (106) and the right edge (109) of the device, solvent transported through the right-center pathway to the junction with the right-hand pathway reaches that point prior to the solvent flowing "downstream" along the right-hand pathway. The solvent then flows "upstream" toward the first end (94) of the right-hand pathway mixing the third and fourth reagents impregnated respectively at the fourth (98) and fifth zones (99) before meeting the downstream flow through the righthand transport pathway. The net solvent flow "downstream" then transports the third and fourth reagents toward the third zone (97). Meanwhile, solvent flow through the right-center pathway has served to prevent the sample and first reagent from flowing back and mixing with the third and fourth reagents.

Chromatographic solvent transport continues with the sample and first reagent transported toward the third zone (97). At the third zone (97), the second immobilized reagent selectively reacts with analyte present in the sample so as to immobilize it. Nonanalyte components of the sample are transported away from the third zone (97). The first reagent then contacts the third zone (97) where it is immobilized against solvent transport by the analyte when the analyte is in immobilized form. At the same time, the chromatographic solvent progressing along the right-hand solvent transport pathway transports the third and fourth reagents to the third zone after any unbound first reagent material is transported past the third zone (97). At the third zone (97), the third and fourth reagents are capable of reacting with any immobilized first reagent to produce a detectable signal. Where a dye compound such as a diazonium salt is used as a third or fourth reagent, the color signal can be a colored complex which is often insoluble in the chromatographic solvent used such that the reacted dye will be immobilized at the third zone (97).

The device is designed such that it is of sufficient length that the chromatographic solvent will not reach the second end (101) and chromatographic solvent transport will continue until the sample and the first, third and fourth reagents have contacted the third zone. In order to determine if the chromatographic solvent has progressed the full length of the device, a sixth zone (100) may be located near the second end (101) of the device. The zone may be impregnated with a fifth reagent which may be a material such as copper sulfate which will indicate the presence of solvent. Thus, when the sixth zone provides a signal that the solvent has progressed the entire length of the device, the third zone is ready for observation to detect either a positive or negative reaction.

Description of the Chromatographic Strip Materials

Chromatographic strip materials useful with the present invention include those materials having capillarity and the capacity for chromatographic solvent transport of non-immobilized reagents and reactive sample components by means of a selected chromatographic solvent. While a wide variety of chromatographic substrate materials such as are used for paper chromatography are suitable for use with the invention, the use of thin layer chromatography substrates is preferred for use with the invention as the use of such substrates improves the speed and resolution of the assays according to the invention. The materials should preferably be inert and generally not react physically or chemically with any of the analytes, reagents or reaction products. The materials may include fibrous materials suitable for use with paper chromatography techniques including woven and non-woven fabrics. More preferred are those materials with microporous or microgranular structures with microporous or microgranular materials suitable for use with thin layer chromatography being particularly preferred.

Thin layer chromatographic materials particularly suitable for the present invention include granular thin layer chromatographic materials such as silica or microgranular cellulose. Preferred nongranular microporous materials include microporous cellulose esters, for example, esters of cellulose with an aliphatic carboxylic acid, such as an alkane carboxylic acid, having from 1 to 7 carbon atoms, e.g., acetic acid, propionic acid, or any of the butyric acids of valeric acids. Especially preferred are microporous materials made from nitrocellulose, by which term any nitric acid ester of cellulose is intended. Suitable materials include nitrocellulose in combination with any of the said carboxylic acid cellulose esters. Thus, pure nitrocellulose esters can be used as consisting of an ester of cellulose having approximately 3 nitric groups per 6 carbon atoms. Most preferred is a mixed acetate/nitrate cellulose ester material under the trade name "Millipore Type HAWP" (Millipore Corp., Bedford, Mass.) which has a pore size of 0.45 $\mu$m.

The various chromatographic materials may be used as such in suitable shapes such as films, strips or sheets. They may also be coated onto or bonded or laminated to appropriate inert support materials such as paper, glass, plastic, metal or fabrics. (One preferred inert support material is Mylar.) Such a support material not only has the effect of providing structural support to the chromatographic material but also prevents evaporation of reagent and solvent materials during the assay procedure. The porous solid substrate is preferably in the form of strips of thickness in the range of from about 0.01 mm to about 0.5 mm, and most preferably of about 0.1 mm. The strips may vary widely in their other dimensions but are preferably kept fairly small in order to shorten the assay development time and minimize material usage. When the strips are extremely small in size they may be attached to a suitable handle or holder in order to aid in handling and observation of results. Strips approximately 3 mm wide and up to 75 mm long have been found to be particularly suitable in the fabrication of single pathway devices according to the present invention. Multiple pathway devices may utilize larger strips onto which multiple pathways are fashioned. The pore size may vary within wide limits but is preferably between about 0.05 $\mu$m and 10 $\mu$m, especially between about 0.1 $\mu$m and 1.0 $\mu$m and most preferably about 0.45 $\mu$m The combination of pore size and substrate thickness may be varied according to the characteristics of the specific reagents used in order to obtain desired properties of speed and resolution.

It is desired that in forming the shapes of the materials of the present invention that any irregularities in the materials or in the edges of the materials which might cause uneven flow through the material be avoided. Preferred means of fashioning the strip materials include the use of a paper cutter with a tungsten carbide rotary blade. Other suitable means include methods such as laser cutting which is particularly suitable for use in mass production.

Because the strip material of the device is preferably chemically inert, it may have to be activated at the third zone in order that the second reagent may be immobilized against solvent transport at that zone. Various methods will be required to render the second reagent immobilized according to the particular chemical nature of the strip material and the second reagent. Generally, when the strip material is nitrocellulose or a mixed nitrocellulose ester no special chemical linkage is required for the immobilization of the second reagent. Various techniques may be used for other materials and reagents which include functionalization with materials such as carbonyldiimidazole, glutaraldehyde or succinic acid, or treatment with materials such as cyanogen bromide. Other suitable reactions include treatment with Schiff bases and borohydride for reduction of aldehydic, carbonyl and amino groups. DNA, RNA and certain antigens may be immobilized against solvent transport by baking onto the strip material. Baking may be carried out at temperatures ranging from about 60° C. to about 120° C. for times varying from about five minutes to about 12 hours, but preferably at about 80° C. for about two hours.

Description of the Antibodies

Antibodies useful in conducting the immunoassays of the present invention include those specifically reactive with various analytes the detection of which in biological fluids is desired. Such antibodies are preferably IgG or IgM antibodies or mixtures thereof, which are essentially free of association with antibodies capable of binding with nonanalyte molecules. The antibodies may be polyclonal or monoclonal and are commercially available or may be obtained by mouse ascites, tissue culture or other techniques known to the art. A typical description of hybridoma procedure for the production of monoclonal antibodies may be found in Wands, J. R., and V. R. Zurawski, Gastroenterology 80:225 (1981); MarshakRothstein, A., et al.; J. Immunol. 122:2491 (1979); Oi, V. Y. and L. A. Herzenberg, "Immunoglobulin Producing Hybrid", Mishell, B. B. and S. M. Shiigi (eds.) Selected Methods in Cellular Immunology, San Francisco: W. H. Freeman Publishing, 1979; and U.S. Pat. No. 4,515,893 issued to Kung, et al. The use of mixtures of monoclonal antibodies of differing antigenic specificities or of monoclonal antibodies and polyclonal antibodies may be desired. Regardless of the particular source or type of antibodies, however, it is preferred that they be generally free of impurities. The antibodies may be purified by column chromatographic or other conventional means but are preferably purified according to known affinity purification techniques.

Description of the Antigens

Antigens useful in carrying out the immunoassays of the present invention include those materials, whether natural or synthesized, which present antigenic determinants for which the analyte antibodies are specifically reactive when presented on the chromatographic strip materials of the invention. Synthesized antigens include those which are constructed according to conventional chemical synthesis as well as those constructed according to recombinant DNA techniques. Antigen materials may be utilized as a reaction material bound to the reaction zone in sandwich assays for the detection of specific antibodies. They may also be labelled and utilized in the same assays as signal molecules for the detection of immobilized antibodies.

Description of Blocking Agents for Immunoassays

Blocking agents useful in preparation of devices for immunoassays of the present invention include those capable of blocking excess binding sites on the chromatographic strip material which might hinder chromatographic solvent transport of sample materials or reagents of the invention. In the construction of devices of the present invention, the second reagent is first immobilized at the third zone. Once the second reagent has been immobilized at the third zone, the strip is then processed so as to block excess binding sites of the chromatographic material which might interfere with chromatographic solvent transport of reagents or sample materials. Particularly suitable is the use of blocking solutions comprising non-specific proteins such as are present in gelatin or total serum. Such proteins are selected to not interfere with or cross-react with reagent materials of the assays. Blocking of the sites may be conducted by treatment with a serum solution such as 3% bovine serum albumin (BSA) in physiological saline. The strips are then incubated for up to 2 hours at a temperature ranging from 30° C. to 50° C., preferably at 40° C., and washed with physiological saline. A preferred blocking material for immunological assays, however, is a gelatin solution such as a 1% LB gelatin solution which requires no incubation.

Description of the Solvent System for Immunoassays

Suitable chromatographic solvent systems for immunoassays according to the present invention include solvents capable of solubilizing the analyte, first reagent and any additional reagents and materials and transporting them to the third zone. Such solvents should have sufficient ionic strength to prevent electrostatic interaction of the transported materials with the strip material. A preferred solvent for use in immunoassay procedures according to the invention is physiological saline solution with a pH in the neutral range. Proteins as well as detergents such as sodium dodecyl sulfate (SDS), Triton X-100 and sodium deoxycholate (DOC) may be incorporated in the chromatographic solvent in quantities which minimize non-specific binding with the strip material but not such excesses as would prevent the desired binding and immobilization reactions. Other chromatographic solvents such as high performance liquid chromatography (HPLC) solvents and high performance thin layer chromatography (HPTLC) solvents which favor solubilization of proteins and other reactants and minimize binding to strip materials such as nitrocellulose may also be used. Parekh, et al., Anal. Biochem., 148, 87–92 (1985) discloses various chromatographic solvents such as solutions of 50% pyridine or 40% acetonitrile in ammonium acetate buffer (pH 8.9) which are particularly suitable with immunoassays according to the present invention.

Description of DNA and RNA Hybridization Materials

DNA and RNA hybridization materials useful according to the present invention include labelled and unlabelled DNA and RNA polynucleotide probes having base sequences generally complementary to those of analyte gene materials. The probes of the invention will generally have between about 25 and about 10,000 bases and preferably between about 30 and about 5,000 bases. The probes need not be perfectly complementary to the base sequences of analyte gene materials and will generally hybridize provided about 70% or greater homology exists between the base sequences. Conditions relating to DNA and RNA hybridization are disclosed generally in Crosa, et al., J. Bact. 115(3), 904–911 (1973). Polynucleotide probe materials may be obtained according to techniques well known in the art. See e.g.

Kornberg, DNA Replication, W. H. Freeman and Co., San Francisco, 670–679 (1978); Dallas, et al., J. Bacteriol. 139, 850–858 (1979) and So, et al., Nature, 277, 453–456 (1979).

According to one hybridization sandwich assays procedure of the present invention, the first zone of the assay device is impregnated with a first reagent, which may be labelled, comprising a polynucleotide probe with a base sequence generally complementary to a first portion of the base sequence of the analyte nucleic acid. At the third zone is immobilized a second reagent comprising a polynucleotide with an exposed base sequence generally complementary to a second portion of the base sequence of the analyte nucleic acid. According to the assay procedure, the analyte containing sample is applied to the second zone and is chromatographically transported to the third zone under hybridization conditions such that analyte material is immobilized by hybridization of the second portion of its base sequence to the base sequence of the second reagent. The first reagent is then chromatographically transported under hybridization conditions to the third zone where it is immobilized by hybridization of its base sequence with the base sequence of the first portion of the analyte molecule base sequence. The relative mobility of the sample components and the first reagent or the site relationship between the second and third zones is such that the analyte is disposed and immobilized against solvent transport at the third zone prior to the first reagent reaching the third zone. Further, interfering sample components and non-analyte components of the sample which are capable of reaction with the first reagent are cleared from the third zone prior to chromatographic transport of the first reagent to the third zone.

Description of Blocking Agents for Hybridization Assays

Blocking agents suitable for use in the polynucleotide hybridization assays according to the present invention include those blocking agents capable of limiting or blocking excess binding sites on the chromatographic strip material which might hinder chromatographic solvent transport of the sample materials or reagents of the invention. Further, such materials should not interfere with hybridization of the sample and reagent polynucleotide materials of the invention. A preferred blocking agent for hybridization assays is a solution comprising SSPE buffer (itself comprising 0.9 M NaCl, 560 mM $NaH_2PO_4$ and 5 mM ethylene diamine tetraacetic acid (EDTA) (pH 7.4) and Denhardt's solution (comprising 0.1% Ficoll, 0.1% polyvinylpyrrolidone and 1 mg/ml BSA). Nitrocellulose strips to which the second reagent has been immobilized are blocked by treatment with this solution in sealed bags for 2 hours at 65° C.

Description of Solvent System for Hybridization Assays

Suitable chromatographic solvent systems for polynucleotide hybridization assays according to the present invention include solvents capable of solubilizing the analyte, first reagent and any additional reagents and materials and transporting them to the third zone. A preferred solvent for use in polynucleotide hybridization assays according to the present invention comprises SSPE buffer (itself comprising 0.9 M NaCl, 560 mM $NaH_2PO_4$ and 5 mM EDTA (pH 7.4)), Denhardt's solution (comprising 0.06% Ficoll, 0.06% polyvinylpyrrolidone and 0.6 mg/ml BSA) and 50% deionized formamide. The preferred solvent ay optionally include carrier DNA such as 100 μg/ml human placental DNA or salmon sperm DNA.

Pathway Manipulation and Solvent Barriers

Various means are known for achieving the sequential transport of reagents and sample materials according to the invention. Such means may include placement of sample materials and reagents, variation of the length of the pathways along which reagents and sample materials are transported and manipulation of the speed at which such transport takes place. Means for varying the pathway distances include forming convoluted pathways through the use of solvent barriers.

Solvent barriers which block chromatographic flow according to the invention may be formed by various physical or chemical etching techniques. Gaps of less than 0.1 mm in width have been found to prevent the flow of liquid. A preferred means for forming such gaps, however, involves the use of laser etching techniques. A $CO_2$ laser may be used according to one procedure wherein Mylar backed nitrocellulose is mounted on a supporting fixture which is mounted on a computer controlled X-Y table capable of very close positioning tolerances. Alternatively, a beam moving mechanism may be used. Using a combination of suitable optical lenses and careful beam focusing, a laser beam spot, with a diameter of approximately 0.005 inches, can be focused on the nitrocellulose. By careful control of the laser power, a narrow path of nitrocellulose, approximately 0.005 inches wide can either be removed from or melted to the Mylar backing.

The use of a $CO_2$ laser is particularly preferred because of the favorable coupling effect of light from the laser with the nitrocellulose. Nevertheless, other types of lasers are suitable, provided that the laser beam wavelength produces the desired effect on the solvent transport material. Through use of a moving beam or an X-Y table, precision paths baffled channels or other intricate shapes may be generated on the nitrocellulose.

Mechanical and chemical means may be used in order to effectively lengthen or shorten the pathways by modifying the chromatographic transport rates of the solvents, reagents and sample materials. A suitable means involves modifying the hydrophilicity of the chromatographic substrate to varying degrees. The hydrophilicity of the substrate may be varied chemically by adding various materials such as proteins or detergents to the medium or chromatographic solvent which affect the surface tension or viscosity of materials on the strip. Such materials should be compatible with the reaction materials to be transported through the lane which they are transported and can be selectively applied to the appropriate lanes through lithographic and other techniques known to those of skill in the art.

When the strip material does not comprise a thin layer chromatography substrate mechanical means may also be used to modify the porosity of the substrate and hence the speed of chromatographic transport. Compression of porous chromatographic materials such as paper will reduce the size of the pores of the material which will generally increase the diffusion rate of materials through that substrate. By selectively compressing certain lanes to greater or lesser extents and not compressing others, it is possible to program a sequence of chromatographic delivery of reaction materials to the third zone. Materials could be compressed by conventional engraving techniques known to those of skill in the art.

Detection Means

Various means are available for detection of the first reagent at the third zone. Such means generally involve labelling of the first reagent with a signal molecule capable of producing a detectable signal which may be a radiolabel, chromophore, fluorophore or enzyme label. While signal molecules labelled with radioisotopes are particularly effective in emitting detectable signals, their detection requires the use of specialized equipment and presents health and safety difficulties. Particularly preferred is the use of labelled indicator molecules producing detectable signals involving light in the visible spectrum. Particularly suitable is the use of enzyme labels wherein the first reagent molecules are labelled with enzymes or coenzymes which the catalyze reactions activating dye materials which absorb or emit radiation so as to produce a detectable signal.

Enzyme systems useful in signal producing systems in the present invention include alkaline phosphatase, horseradish peroxidase, glucose oxidase, $\beta$-galactosidase and $\beta$-lactamase. Other enzymes and coenzymes useful in signal producing systems include those described in U.S. Pat. No. 4,275,149 (cols. 19–23) and U.S. Pat. No. 4,318,980 (cols. 10–14) the disclosures of which are hereby incorporated by reference. The use of enzymes which produce hydrogen peroxide which then oxidizes a dye precursor to a dye is well known in the art. Suitable combinations include saccharide oxidases such as glucose oxidase and galactose oxidase and heterocyclic oxidases such as uricase and xanthine oxidase in combination with an enzyme such as peroxidase and cytochrome C oxidase to produce hydrogen peroxide and oxidize a dye precursor. The use of other oxidoreductases is also suitable as is the use of enzymes such as hydrolases and transferases. Various coenzymes such as NADH, NADPH, pyridoxal phosphate, FADH and FMNH may be used particularly in conjunction with oxidoreductases.

EXAMPLE 1

In this example, a single pathway immunoassay device for the detection of syphilis antibodies was constructed and used. Microporous nitrocellulose material with a thickness of approximately 0.1 mm and an average pore size of 0.45 $\mu$m was cast onto an inert Mylar support sheet approximately 0.1 mm thick (Micron Separation Industries, Waltham. Mass.). A piece measuring 27 mm by 31 mm was cut with a rotary blade paper cutter (Alvin, Windsor, Conn.) In order to assist in fabrication of the devices a grid was then printed onto the nitrocellulose with an inkjet printer (Hewlett Packard, Thinkjet, Palo Alto, Calif.) utilizing a graphics software package and a Hewlett Packard 9816 computer (Palo Alto, Calif.) The grid comprised a number of numbered lanes approximately 3 mm wide and 31 mm long which were crossed by five lines 3 mm apart, the first line being 9 mm from the first end of the grid. The first and second lines define a first zone, the third line defines the center of a second zone and the fourth and fifth lines define a third zone. A 27 mm by 29 mm Mylar cover plate was then used to overlay the nitrocellulose leaving an uncovered 2 mm tab of nitrocellulose exposed on the first end. Further, 2 mm diameter holes were punched in the nitrocellulose cover corresponding to the second and third zones. In addition, a 9 mm by 27 mm Mylar strip was cut to cover the holes during chromatography. Both pieces of Mylar were coated on one side with rubber cement (Sanford, Bellwood, Ill.) and were allowed to dry for at least one hour.

Syphilis antigen comprising treponema pallidum was isolated by intra-testicular injection of rabbits and was purified by differential centrifugation. The antigen was applied to the third zone in alternate lanes in 0.5 $\mu$l aliquots of a TBS solution comprising the antigen at a concentration of $10^9$ cells per ml with bovine serum albumin at a concentration of 1 mg/ml. Alternate lanes were used so as to prevent material from one lane from contaminating another. The nitrocellulose was then blocked by incubation for one hour at room temperature and gentle agitation with a 1% solution of LB gelatin, (Inotech, Wohlen, Switzerland) in TBS solution comprising (0.15 M NaCl, 0.02 M Tris-HCl, pH 7.6) The sheet was then drained and allowed to air dry.

Peroxidase labelled goat anti-human IgG antibody (Kirkegaard-Perry, Gaithersburg, Md.) was then diluted at a 1:5 ratio in a mixture comprising 1% LB gelatin and 1.0% Triton X-100. The antibody mixture was then applied in 0.5 $\mu$l aliquots to the first zones of the same lanes to which the antigen had previously been applied. The same diluent mixture comprising 1% LB gelatin and 1.0% Triton X-100 was then added in 0.5 $\mu$l aliquots to the second (sample receiving) zones of the devices.

The Mylar support strip and cover sheet were affixed to the treated nitrocellulose such that the second and third zones and 2 mm of the first end were exposed. Positive and negative serum samples were then applied to the second zones in 0.5 $\mu$l aliquots and the sample ports were covered with the previously prepared Mylar strip. The first end of the sheet was then dipped in a solvent comprising TBS and 1% gelatin and the liquid front was allowed to rise to the top of the sheet over a period of approximately 10 minutes. The cover sheet was stripped off leaving the chromatographic material exposed. The third zones of the strips were then immersed for 15 minutes in a peroxidase indicator solution comprising 10 ml TBS, 4 $\mu$l of 30% hydrogen peroxide solution and 0.8 ml of a solution comprising 4-chloronaphthol in methanol at a concentration of 3 mg/ml. Positive sera and the presence of the enzyme labelled antibody resulted in the presence of a blue black spot at the third zone.

EXAMPLE 2

In this example, a single etched pathway device was constructed for the detection of AIDS patient antibodies to HIV (human immunodeficiency virus. The general procedures of Example 1 were used with the exception that nitrocellulose was glued manually to 8 inch by 11 inch Mylar sheets using rubber cement according to the methodology of Example 1. Parallel lines were etched into the nitrocellulose at 3 mm intervals by controlled treatment with a $CO_2$ laser without burning through the backing. (performed by Laser Age, Inc. Waukegan, Ill.) In this example, all lanes were used as there was no liquid flow between channels.

Suitable HIV antigen (see, Gallo, U.S. Pat. No. 4,520,113) was treated with 30% w/v Biobeads (Biorad, Richmond, Calif.) for 30 minutes in order to remove detergent from the preparation. The antigen was then applied to the nitrocellulose according to the methods of Example 1. Peroxidase labelled goat antihuman IgG according to Example 1 was then added to the first zone and the remaining procedures of Example 1 were followed. Tests with positive and negative HIV sera samples gave positive color reactions for the the positive samples and no color reaction for the negative samples.

EXAMPLE 3

In this example, a single pathway immunoassay device for the detection of specific antigens is described. This device is similar in principle to the antibody detection device of Example 1 with the exception that antibodies specifically reactive with the antigen to be detected are immobilized against solvent transport at the third zone of the device where they selectively bind with antigen containing substances of interest in the analyte sample. The antigen materials so immobilized may then be detected by treatment with labelled antibodies specifically reactive with the same or other antigenic epitopes of the antigen of interest.

Microporous solid substrate material, preferably nitrocellulose with a thickness of approximately 0.1 mm is cast onto a Mylar sheet preferably of the same thickness. A grid is then printed onto the nitrocellulose with an inkjet printer comprising a number of lanes approximately 3 mm wide and from about 20 to about 100 mm long and preferably about 75 mm long. Antibody material specifically reactive with one or more antigenic determinants of the antigen to be assayed for is then applied to the third zone of the strips at a position that is near one end of the strip and preferably about 10 mm from one end. The antibody material may be polyclonal or monoclonal antibodies or combinations thereof and may be IgG, IgM or other classes of immunoglobulin or combinations thereof. The antibodies may be applied to the porous substrate by manual means such as capillary tubes, pipettes or liquid propellants. Where the immunoglobulin is applied by means of a spray, a template or applicator miniaturized by means of procedures such as are known in the microelectronics art may be used in conjunction with known lithographic techniques.

The antibodies may be applied to the third zone so as to provide any suitable geometry such as dots, lines or spots. It is preferable that antibody solutions be applied in volumes smaller than 1 $\mu$l with volumes of about 0.5 $\mu$l particularly preferred for producing spots of about 1-2 mm in diameter. Zones of this size are preferred for devices relying upon visual examination of positive color signals. Smaller volumes of antibody solution may also be used but such volumes may produce smaller zones which require evaluation by spectrophotometric means. Where it is contemplated that devices of the present invention be evaluated by nonvisual means such as with a reflectance spectrophotometer it is preferred that volumes smaller than 0.5 $\mu$l be applied so as to further reduce the amounts of antibody materials required for fabrication of the devices of the invention.

Concentrations of antibodies applied in solutions are preferably in the range of about 100-150 $\mu$g of IgM per ml of solution when applied to the nitrocellulose sheets of the present invention. Most preferred are antibody concentrations in the range of about 120-140 $\mu$g of IgM per ml of solution. Greater concentrations can be applied but may not serve to increase the binding efficiency of the third zone. Lessor concentrations may also be applied with the effect that the density of positive binding signals will be diminished. While it is contemplated that lesser antibody concentrations may reduce positive signal intensity to the extent of hindering visual evaluation of test results, it is nevertheless contemplated that reduced binding signal intensity will not unduly hinder spectrophotometric or other techniques for automated evaluations of the devices of the invention.

After addition of the antibody material to the third zone, the third zone and the rest of the strip material is preferably treated with a blocking agent such as a 1% LB gelatin solution. At this time, the first reagent comprising labelled antibody material specifically reactive with one or more antigenic determinants of the analyte is applied to the first zone located between the third zone and the first end. This labelled antibody material is not immobilized against chromatographic solvent transport and is intended to be chromatographically mobile such that it may be transported to the third zone. The first reagent may be applied by means such as capillary tubes, pipettes or liquid propellants. The antibody material may be monoclonal or polyclonal and may be of varying subtype and epitopic specificity so long as it is specifically reactive with the antigen presented by the analyte. The antibody material is labelled such that it may be detected by visual, spectrophotometric or other means. Enzyme linked antibodies which catalyze a detectable color reaction are particularly preferred.

After application of the fixed antibodies to the third zone and the labelled chromatographically mobile antibodies to the first zone, the device may be covered, except at the third zone and optionally at the second zone, with a cover which in one embodiment may be Mylar for from 3 to 5 mm at the end of the strip. The cover prevents the evaporation of chromatographic solvent and any volatile reagents of the device.

In order to use the antigen assay device, the sample which can be serum, or other biological or nonbiological fluids, is applied to the second zone of the device. It is preferred that sample solutions be applied in volumes of 0.1 $\mu$l to 5 $\mu$l with volumes of 1 $\mu$l particularly preferred. Because of differences in antigen concentrations and activities, these volumes may vary although it is well within the ability of one of ordinary skill in the art to determine appropriate volumes.

After application of the sample material, the end of the test device is immersed in a chromatographic solvent solution. One preferred solution comprises a 1% LB gelatin solution although other chromatographic solvents known to the art are equally useful. The solvent progresses through the strip transporting the antibodies of the first reagent slightly behind the solvent front toward the third zone. As the solvent front progresses up the test device it next encounters the sample material which it entrains and transports toward the third zone. The sample material is transported slightly ahead of the solvent front while the first reagent material is transported slightly behind the solvent front. As a consequence the two materials do not mix. Only when the analyte material is immobilized by the second reagent at the third zone does the first reagent overtake the analyte and react therewith. Other material contained in the sample will continue to be chromatographically transported by the solvent and will be removed from the third zone. Where no analyte material is bound to the third zone, the first reagent will continue to be chromatographically transported and will be removed from the third zone thus producing no signal at that zone.

EXAMPLE 4

In this example, a two pathway "diode" device was prepared for the detection of HIV. According to this example, test devices were cut in the general form of the device of FIG. 3 with a high energy laser which cut through both the nitrocellulose and Mylar layers. A second pass with a lower energy beam cut through only the nitrocellulose layer to create two chromatographic solvent transport pathways. The third zone was impregnated with the same HIV preparation described in Example 2 and the first zone was impregnated with the same peroxidase labelled goat anti-human IgG antibody according to the method of Example 2. The devices of this example also comprise fourth and a fifth zones impregnated therewith third and fourth reagents comprising in this case an enzyme substrate compound and a dye compound. The fourth zone was impregnated with a third reagent comprising 0.5 $\mu$l of 0.1 M 5-bromo-4-chloro-3-indolyl phosphate in 0.1 M Tris base while the fifth zone was impregnated with a fourth reagent comprising 0.5 $\mu$l of 0.1 M nitro blue tetrazolium (Sigma) in water. The entire device was then covered with a Mylar cover with a sample port at the second (sample) zone. Positive and negative HIV sera samples were then applied to the second zone and the devices were dipped in solvent comprising 1% LB gelatin and TBS. Positive sera samples gave positive color reactions while negative sera samples gave negative color reactions.

Variations of the device of this example include the "triode" and "tetrode" devices illustrated in FIGS. 4 and 6. The same reagents and materials are incorporated in these devices with the exception that additional channels are etched into the devices. These channels may be used to time mixing and transport of reagents and prevent premature mixing of the reagents and sample materials.

EXAMPLE 5

In this example, a single pathway polynucleotide hybridization assay device is constructed and used. A piece of microporous nitrocellulose material approximately 5 mm wide by 55 mm long with a thickness of approximately 0.1 mm is cast onto an inert Mylar support sheet approximately 0.1 mm thick. The strip is prewetted with SSPE buffer solution comprising 0.9 M NaCl, 560 mM NaH$_2$PO$_4$ and 5 mM EDTA (pH 7.4). To a third zone approximately 27 mm from the first end of the strip is applied about 1.5 $\mu$l of a second reagent solution comprising about 15 picomoles linearized denatured DNA generally complementary to a first portion of the base sequence of the analyte polynucleotide in SSPE buffer comprising 0.9 M NaCl, 560 mM NaH$_2$PO$_4$ and 5 mM EDTA (pH 7.4). The strip is then air dried and baked at 80° C. for 2 hours.

The strip material to which the second reagent has been applied is then prewetted in the SSPE buffer solution and impregnated with a blocking solution comprising the SSPE buffer and Denhardt's solution comprising 0.1 % Ficoll, 0.1% polyvinylpyrrolidone and 1 mg/ml BSA. The strip is placed in a sealed bag for 2 hours at 65° C. and is then air-dried.

The strip is then impregnated at the first zone 7 mm from the first end with about 100 picomoles of a first reagent material comprising a linearized and denatured radiolabelled polynucleotide with a base sequence generally complementary to a second portion of the base sequence of the analyte polynucleotide. The first reagent is labelled at its 5' end by treatment with $^{32}$P radiolabel and T4 polynucleotide kinase. The first reagent material is then air dried and a Mylar cover plate with a gap over a second zone between the first and third zones is placed over the nitrocellulose chromatographic material.

Assays are conducted with the polynucleotide hybridization assay device of the invention by application of analyte containing sample material to the second zone. A cover tab is then placed over the second zone and the assay device is dipped into about 175 $\mu$l of chromatographic solvent comprising SSPE solution (comprising 0.9 NaCl, 560 mM NaH$_2$PO$_4$, 5 mM EDTA (pH 7.4)), Denhardt's solution (comprising 0.06% Ficoll, 0.06% polyvinylpyrrolidone and 0.6 mg/ml BSA), and 50% deionized formamide. While the strip is incubated at 37° C. the solvent progresses upward along the device and solubilizes and chromatographically transports the first reagent toward the third zone. Upon reaching the second zone the chromatographic solvent solubilizes and transports the analyte containing sample toward the third zone. The relative mobility of the first reagent and the sample components is such that the analyte is disposed and immobilized against solvent transport at the third zone prior to the first reagent reaching the third zone. Further, any interfering sample components and non-analyte components of the sample which are capable of reaction with the first reagent are cleared from the third zone prior to chromatographic transport of the first reagent to the third zone.

Upon reaching the third zone, any analyte material within the sample will be immobilized by hybridization at a second base sequence with the second reagent immobilized at that zone. Any non-hybridized material will be cleared from the third zone by chromatographic solvent transport prior to arrival of the first reagent. Upon reaching the third zone, the radiolabelled first reagent will itself be immobilized by hybridization at a first base sequence of the analyte. The strip and chromatographic solvent are incubated at 37° C. until the solvent front reaches the top of the strip at which time the strip is removed from the solvent and air-dried. The strip is then subjected to autoradiography with Kodak XAR-5 film. The presence of analyte in the sample material will be indicated by exposure of film contacted at the third zone. Variations of the device of this example include "diode", "triode" and "tetrode" devices utilizing enzyme labels and detection systems.

Numerous modifications and variations in practice of the invention are expected to occur to those skilled in the art upon consideration of the foregoing descriptions of preferred embodiments thereof. Consequently, only such limitations should be placed on the invention as appear in the following claims.

What is claimed is:

1. A test strip for analysis of an analyte in a sample by means of a sequential series of reactions, said strip comprising:

a length of chromatographic material having capillarity and the capacity for chromatographic solvent transport of non-immobilized reagents and reactive sample components by means of a selected chromatographic solvent, said strip including, a first end at which chromatographic solvent transport begins;

a second end, at which chromatographic solvent transport ends;

a plurality of chromatographic solvent transport pathways;

a plurality of zones positioned between said first and second ends, said zones including, a first zone impregnated with a first reagent which is mobile in said solvent and capable of a specific binding reaction with said analyte, a second zone for receiving said sample, and a third zone, downstream of said second zone, impregnated with a second reagent which is immobilized against solvent transport and is capable of a specific binding reaction with the analyte so as to immobilize the analyte in said third zone, said first and second zones being spaced sufficiently from said first end to permit contact of said first end but not said first and second zones with said chromatographic solvent, and means for detecting said first reagent at said third zone as a measure of the analyte, whereby, after said first end is dipped into said chromatographic solvent, the relative mobility of said sample components and said first reagent is controlled by said plurality of chromatographic solvent transport pathways such that the analyte is transported to and immobilized against solvent transport at the third zone prior to the first reagent reaching the third zone, and whereby interfering sample components and non-analyte components of the sample which are reactive with said first reagent are cleared from said third zone by chromatographic solvent transport prior to the first reagent reaching said third zone.

2. The test strip according to claim 1 wherein said means for detecting said first reagent at said third zone is a label on said first reagent.

3. The test strip according to claim 2 wherein said label is selected from the group consisting of radiolabels, chromophores, fluorophores and enzyme labels.

4. The test strip according to claim 1 wherein the chromatographic solvent transport pathways of said sample and of said first reagent are partially non-coincident.

5. The test strip according to claim 3 wherein said label is an enzyme label and a third reagent reactive with said label is disposed at a fourth zone and has a relative mobility in said chromatographic solvent such that the third reagent is transported to said third zone by said solvent after said first reagent is transported to said third zone.

6. The test strip according to claim 5 wherein said third reagent is an indicator substance.

7. The test strip according to claim 5 wherein the chromatographic solvent transport pathways of said first reagent and said third reagent are partially non-coincident.

8. The test strip according to claim 1 wherein said chromatographic solvent transport pathways are separated by means of solvent impermeable barriers.

9. The test strips according to claim 8 wherein said solvent impermeable barriers are formed by laser etching.

10. The test strips according to claim 1 wherein said chromatographic material is thin layer chromatographic material.

11. The test strips according to claim 10 wherein said thin layer chromatographic material is nitrocellulose.

12. The test strips according to claim 1 wherein said analyte is an antibody.

13. The test strips according to claim 1 wherein said analyte is an antigen.

14. The test strips according to claim 1 wherein said analyte is a polynucleotide.

15. A method for analysis of analyte in a sample by means of a sequential series of reactions, said method employing:

a strip comprising a length of chromatographic material having capillarity and the capacity for chromatographic solvent transport of non-immobilized reagents and reactive sample components by means of a selected chromatographic solvent, said strip including, a first end at which chromatographic solvent transport begins;

a second end, at which chromatographic solvent transport ends;

a plurality of chromatographic solvent transport pathways;

a plurality of zones positioned between said first and second ends, said zones including, a first zone impregnated with a first reagent which is mobile in said solvent and capable of a specific binding reaction with said analyte, a second zone for receiving said sample, and a third zone, downstream of said second zone, impregnated with a second reagent which is immobilized against solvent transport and is capable of a specific binding reaction with the analyte so as to immobilize the analyte in said third zone, said first and second zones being spaced sufficiently from said first end to permit contact of said first end but not said first and second zones with said chromatographic solvent, and means for directing said first reagent at said third zone, said method comprising:

(1) disposing said sample in said second zone; (2) dipping said first end into chromatographic solvent for a time sufficient to chromatographically transport said analyte and said first reagent to said third zone, wherein the relative mobility of said sample components and said first reagent is controlled by said plurality of chromatographic solvent transport pathways such that the analyte is transported to and immobilized against solvent transport at the third zone prior to the first reagent reaching the third zone, and whereby interfering sample components and non-analyte components of the sample which are reactive with said first reagent are cleared from said third zone by the chromatographic solvent transport prior to the first reagent reaching said third zone; and (3) detecting the presence of said first reagent in said third zone as a measures of the analyte.

16. A method according to claim 15 wherein said means for detecting said first reagent at said third zone is a label on said first reagent.

17. A method according to claim 15 wherein said means for detecting said first reagent at said third zone is a third reagent reactive with said first reagent.

18. A method according to claim 17 wherein the third reagent is an indicator substance.

19. A method according to claim 17 wherein said third reagent is disposed at a fourth zone and is chromatographically transported to said third zone after said first reagent is transported to said third zone.

20. A method according to claim 19 wherein said first reagent and said third reagent are transported along pathways of travel which are partially noncoincident.

21. A method according to claim 19 wherein said sample and said third reagent are transported along pathways of travel which are partially non-coincident.

22. A method according to claim 15 wherein said chromatographic solvent pathways are partially noncoincident as a result of solvent impermeable barriers.

23. A method according to claim 15 wherein said chromatographic material is thin layer chromatographic material.

24. A method according to claim 23 wherein said thin layer chromatographic material is nitrocellulose.

25. A method according to claim 24 wherein said nitrocellulose is characterized by an average pore size ranging from about 0.1 micron to about 1 micron.

26. A method according to claim 15 wherein said analyte is an antibody.

27. A method according to claim 15 wherein said analyte is an antigen.

28. A method according to claim 15 wherein said analyte is a polynucleotide.

29. A method for analysis of analyte in a sample by means of a sequential series of reactions, said method employing:
a strip comprising a length of chromatographic material having capillarity and the capacity for chromatographic solvent transport of non-immobilized reagents and reactive sample components by means of a selected chromatographic solvent, said strip including,
a first end at which chromatographic solvent transport begins;
a second end, at which chromatographic solvent transport ends;
a plurality of zones positioned between said first and second ends, said zones including,
a first zone impregnated with a first reagent which is mobile in said solvent and capable of a specific binding reaction with an analyte,
a second zone for receiving said sample, and
a third zone, coincident with said second zone, impregnated with a second reagent which is immobilized against solvent transport and is capable of a specific binding reaction with the analyte so as to immobilize the analyte in said third zone, said first and second zones being spaced sufficiently from said first end to permit contact of said first end but not said first and second zones with said chromatographic solvent, and
means for detecting said first reagent at said third zone as a measure of the analyte,
said method comprising:
(1) disposing said sample in said second zone; (2) dipping said first end into said chromatographic solvent for a time sufficient to chromatographically transport said first reagent to said third zone, whereby after said first end is dipped into said chromatographic solvent, the relative mobility of said sample components and said first reagent is such that the analyte is immobilized against solvent transport at the third zone prior to the first reagent reaching the third zone, and whereby interfering sample components and non-analyte components of the sample which are reactive with said first reagent are cleared from said third zone by chromatographic solvent transport prior to the first reagent reaching said third zone, and (3) detecting the presence of said first reagent in said third zone as a measure of the analyte.

30. A method according to claim 29 wherein said means for detecting said first reagent at said third zone comprises a third reagent reactive with said first reagent.

31. A method according to claim 30 wherein said third reagent is disposed at a fourth zone and is chromatographically transported to said third zone after said first reagent is transported to said third zone.

32. A method according to claim 31 wherein said first reagent and said third reagent are transported along pathways of travel which are partially non-coincident.

33. A method according to claim 29 wherein said chromatographic material comprises thin layer nitrocellulose.

* * * * *